(12) United States Patent
Jiang et al.

(10) Patent No.: US 8,778,896 B2
(45) Date of Patent: *Jul. 15, 2014

(54) LEVOISOVALERYLSPIRAMYCIN I, II OR III, PREPARATIONS, PREPARATION METHODS AND USES THEREOF

(75) Inventors: Yang Jiang, Liaoning (CN); Yuyou Hao, Liaoning (CN)

(73) Assignee: Shenyang Tonglian Group Co., Ltd., Liaoning (CN)

( * ) Notice: Subject to any disclaimer, the term of this patent is extended or adjusted under 35 U.S.C. 154(b) by 16 days.

This patent is subject to a terminal disclaimer.

(21) Appl. No.: 13/699,459

(22) PCT Filed: May 25, 2011

(86) PCT No.: PCT/CN2011/074644
§ 371 (c)(1),
(2), (4) Date: Nov. 21, 2012

(87) PCT Pub. No.: WO2011/147313
PCT Pub. Date: Dec. 1, 2011

(65) Prior Publication Data
US 2013/0065848 A1     Mar. 14, 2013

(30) Foreign Application Priority Data

| May 25, 2010 | (CN) | 2010 1 0182108 |
| May 25, 2010 | (CN) | 2010 1 0182109 |
| May 25, 2010 | (CN) | 2010 1 0182111 |

(51) Int. Cl.
*A61K 31/70* (2006.01)
*C07H 17/08* (2006.01)
*C12P 19/62* (2006.01)
*C12N 9/10* (2006.01)

(52) U.S. Cl.
CPC ............. *C07H 17/08* (2013.01); *C12P 19/62* (2013.01); *C12N 9/1029* (2013.01)
USPC .................. 514/30; 536/7.1; 435/76

(58) Field of Classification Search
USPC ............................................. 536/7.1; 435/76
See application file for complete search history.

(56) References Cited

FOREIGN PATENT DOCUMENTS

| CN | 1174238 A | 2/1998 |
| CN | 1405299 A | 3/2003 |
| CN | 1554355 A | 12/2004 |
| CN | 10773510 A | 7/2010 |
| CN | 101785778 A | 7/2010 |
| CN | 101785779 A | 7/2010 |

OTHER PUBLICATIONS

International Search Report (PCT/ISA/210) issued on Sep. 8, 2011, by the Chinese Patent Office as the International Searching Authority for International Application No. PCT/CN2011/074644.

*Primary Examiner* — Elli Peselev
(74) *Attorney, Agent, or Firm* — Buchanan Ingersoll & Rooney PC

(57) ABSTRACT

Disclosed are levoisovalerylspiramycin I, II or III, preparations, preparing methods and uses thereof. The preparations comprise levoisovalerylspiramycin I, II or III and pharmaceutically acceptable carrier and/or adjuvant, wherein the purity of levoisovalerylspiramycin I, II or III is above 90 wt %. The levoisovalerylspiramycin I, II or III has a good antibacterial activity, and the preparations include solution for injection, powder for injection or lyophilized powder for injection.

17 Claims, 3 Drawing Sheets

LEVOISOVALERYLSPIRAMYCIN I, II OR III, PREPARATIONS, PREPARATION METHODS AND USES THEREOF

FIELD OF THE INVENTION

The invention relates to a new macrolide antibiotics of genetic engineering, in particular, to levoisovalerylspiramycin I, II or III, and crystals, pharmaceutical preparation and preparing methods thereof, as well as uses in anti-infection drugs.

BACKGROUND OF THE INVENTION

Macrolide antibiotics play an important role clinically as they have good activity against gram-positive bacteria, and some gram-negative bacteria as well and have good antibacterial activity and tissue permeability for uncontrollable causative agents such as some increasingly epidemic toxoplasm and *legionella*. Featured by fast absorption by oral administration, few adverse reactions, macrolide antibiotics basically have no effect on the liver and kidney but have potential immunoregulation function. In the nineties, macrolide antibiotics were thought to be a competitor for β-lactam drugs in treating respiratory tract infection of adults.

Chirality is a basic attribute of three-dimensional body and one of the essential attributes of nature. Biological macromolecules including protein, polysaccharide, nucleic acid and enzyme as important basis of vital movement often have important physiological functions. Chiral drug is a pair of enantiomers of material object and mirror image obtained after molecular structure of drug is introduced into the chiral center. These enantiomers are basically the same regarding physicochemical properties but different in optical activity. The enantiomers are respectively named R-type (dextrorotatory) or S-type (sinistral), and racemic. In recent 20 years, as pharmaceutical research is more intensive, it has been proved that the difference of drug enantiomer's affinity with receptor caused by the difference of drug enantiomer's stereoselectivity leads to great difference in pharmacological action. Enantiomer with high activity among chiral drugs is called eutomer; while the one with low or no activity is called distomer. In many cases, the distomer not only has no pharmacological action, but also offset that of eutomer. Sometimes, severe toxic side reactions will occur, showing the complexity of difference in pharmacological function and determining great difference in the therapeutic index of single enantiomer and the racemate thereof. For example, the curative effect of well-known DL-(+−) syntomycin is half of D(−) chloramphenicol; the pharmaceutical activity of propranolol L-isomer is 100 times larger than that of D-isomer; (−) adanon is a strong painkiller while (+) is non-effective. There is also difference in toxicity. For example, the two enantiomers of thalidomide have similar sedation for mice, but only S(−) isomer and metabolin thereof have embryotoxin and teratogenesis; ketamine is a widely used anaesthetic and analgesic, but has side effects such as hallucinating. Studies show that S (+) is 3~4 times more effective than R(−) and toxic side effects have something to do with the latter. The great difference of chiral drug's curative effect has promoted the research and development of chiral drugs and the development separation analysis. By using "chiral" technology, we can remove those with no effect or toxic side effects from drugs effectively and produce pure chiral drugs with single and oriented structure, thus making more pure pharmaceutical ingredients, further quickening curative effect and shortening the course of treatment. Therefore, research on chiral drugs has become one of the new methods for new medicine research worldwide. National governments and pharmaceutical enterprises have invested heavily in fields such as preparations of chiral drug, chiral materials and chiral intermediate for research and development, for the purpose of seizing dominance of chiral pharmacy market. Besides, with continuous improvement of chiral technology, especially the fast and wide use of liquid chromatography, the separation analysis and determination of enantiomers of chiral drugs are promoted. Chiral drugs of single enantiomer have been widely used.

Carrimycin is a new derivative of spiramycin developed by adopting genetic engineering technology, which is originally named biotechspiramycin and formerly named biotechmycin [Patent No.: ZL97104440.6]. According to the "Rules for Chinese Approved Drug Names", and upon technical review and confirmation of Chinese Pharmacopoeia Commission, the generic name of biotechspiramycin is changed to carrimycin. The chemical structure of carrimycin mainly comprises 4"-isovalerylspiramycin, including 4"-isovalerylspiramycin I, II, III, and about 6 4"-hydroxy acylated spiramycin, so the chemical name is 4"-acylspiramycin.

Chemical structural formula of carrimycin is as shown in formula (1):

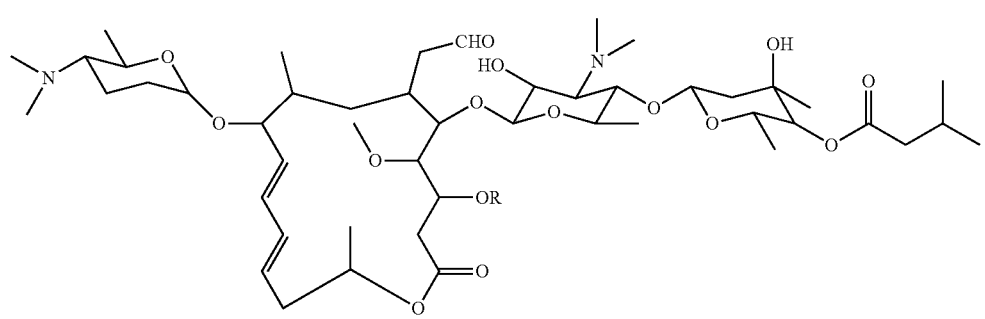

(1)

Wherein: R in isovalerylspiramycin I is from H;
R in isovalerylspiramycin II is from COCH$_3$, R in isovalerylspiramycin III is from COCH$_2$CH$_3$.

Carrimycin is a 16-membered ring macrolide antibiotic, which inhibits the protein synthesis by combining with ribosome of bacterium.

Pharmacokinetics study shows that effective components of carrimycin with activity are mainly isovalerylspiramycin I, II and III. Carrimycin quickly metabolizes to spiramycin in vivo. According to AUC$_{0-t}$ of parent drug isovalerylspiramycin I, II and II and active metabolite spiramycin I, II and III, the absolute bioavailability by oral administration is 91.6% averagely. It is reported that the absolute bioavailability of spiramycin by oral administration is 30~40% (Frydman A M et al J Antimicrob Chemother. 1988, 22(suppl B):93-103). It shows that the isovalerylspiramycin apparently improves the bioavailability of active component spiramycin. Single dose carrimycin is eliminated slowly. $T_{1/2}$ is between 23~27 hours.

In vitro test results show that carrimycin is effective against gram-positive bacteria, especially some drug-resistance bacteria such as β-lactam resistance *staphylococcus aureus* and erythrocin-resistance *staphylococcus aureus*, and has no apparent cross resistance with similar drugs. Meanwhile, carrimycin has antibacterial activity for mycoplasma and chlamydia, as well as some gram-negative bacteria, has good antibacterial activity and tissue permeability for epidemic toxoplasm and *legionella*, and still has potential immuno-regulation function. The antibacterial activity in vivo is much better than that in vitro (ZL200310122420.9). Clinical research shows that by taking carrimycin tablets 200 mg~400 mg everyday for 5~7 days, it is suitable for treating acute bacterial pharyngitis and acute suppurative tonsillitis caused by pyogenic streptococcus; bacterial nasosinusitis and acute bronchitis caused by sensitized bacteria; mild pneumonia caused by *streptococcus pneumonia, haemophilus influenza* and *mycoplasma pneumonia*; nongonoccal urethritis caused by mycoplasma and chlamydia; infectious diseases such as skin and soft tissue infection, periodontitis and otitis media caused by sensitized bacteria. The total effective rate is 92.68%.

Clinical research proves that carrimycin is an antibiotic safe and effective by oral administration. However, as carrimycin is a product obtained through fermentation and is a multicomponent drug, it is very difficult to further separate and purify multicomponent drugs. The current HPLC can separate the multiple acylspirmycins in carrimycin sample, for example, the separation degree of isovalerylspiramycin II and isobutyrylspiramycin III, isobutyrylspiramycin II and propionylspiramycin III, propionylspiramycin III and said component, propionylspiramycin II and acetyl spiramycin III is higher than 1.5 as stipulated in Chinese Pharmacopoeia, while that of acetyl spiramycin III and said component is 1.2.

Through lots of researches and adjustment and optimization of culturing and fermentation conditions, the inventor gets a levocarrimycin, which has better anti-infection activity.

At present, HPLC is employed and it is determined that carrimycin comprises 9 acylspiramycin components, including isovalerylspiramycin (I+II+III), which should not be less than 60% in total, and acylspiramycin, which should not be less than 80% in total. It is quite hard to meet the quality control standard of injection for multicomponent antibiotics produced through fermentation, but injection takes effect quickly for critical patients and those who should not take medicine orally, thus single-component preparation of isovalerylspiramycin is of profound significance. In the present invention, through further research on levocarrimycin, single component of levoisovalerylspiramycin I with purity as high as 98 wt % is obtained.

SUMMARY OF THE INVENTION

A first object of the present invention is to provide levoisovalerylspiramycin I, levoisovalerylspiramycin II and levoisovalerylspiramycin III.

It is a second object of the present invention to provide preparation containing levoisovalerylspiramycin I, levoisovalerylspiramycin II and levoisovalerylspiramycin III respectively.

It is a third object of the present invention to provide a method for preparing levoisovalerylspiramycin I, levoisovalerylspiramycin II and levoisovalerylspiramycin III.

It is a fourth object of the present invention to provide uses of levoisovalerylspiramycin I, levoisovalerylspiramycin II and levoisovalerylspiramycin III.

It is a fifth object of the present invention to provide crystals of levoisovalerylspiramycin I, levoisovalerylspiramycin II and levoisovalerylspiramycin III, as well as preparation containing the crystals respectively.

In order to realize the purposes of the present invention, the following technical scheme is employed:

The present invention relates to a levoisovalerylspiramycin I compound, the chemical structural formula of which is shown as formula (I):

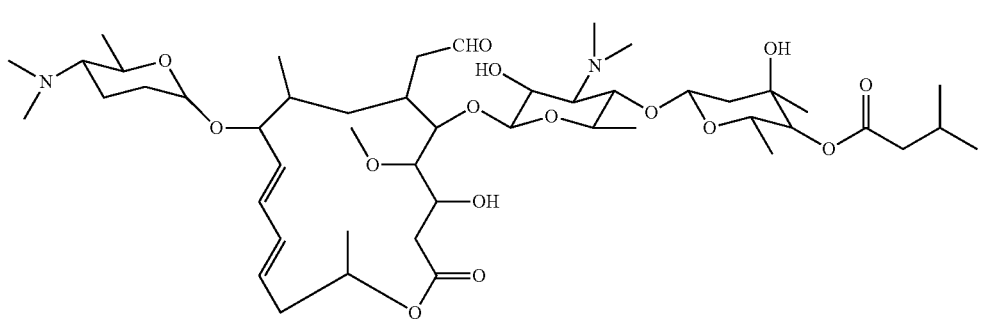

The specific optical rotation $[\alpha]_D$ is −49°~−62°, preferably, −51°~−60°, −α°~−62°, further preferably −51°~−58°, −53°~−58°, further preferably −55°~−58°, −55°~−57°, −58°~−60°, −51°~−−55°, further preferably −53°~−55°, further preferably −49°~−51° (C=0.02 g/ml, CHCl₃, 25□, λ=589.3 nm); and the melting point is 116~122□, preferably, 118~120□;

The present invention relates to a levoisovalerylspiramycin II compound, the chemical structural formula of which is shown as formula (II):

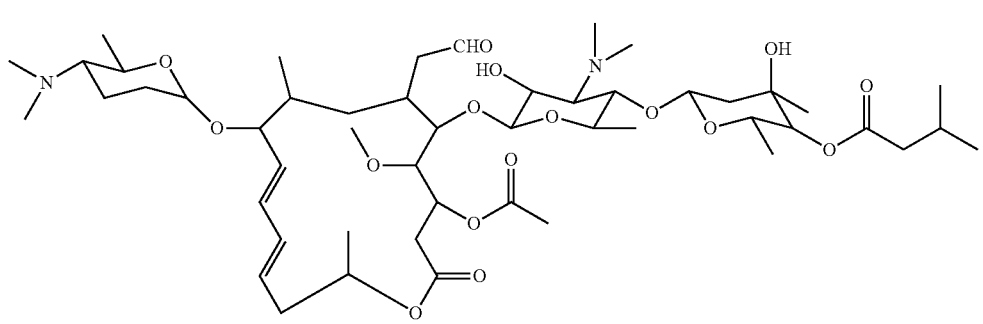

The specific optical rotation $[\alpha]_D$ is 55°~−61°, preferably, −57°~−59° (C=0.02 g/ml, CHCl₃, 25□, λ=589.3 nm); and the melting point is 120~128□, preferably, 123~125□;

The present invention relates to a levoisovalerylspiramycin III compound, the chemical structural formula of which is shown as formula (III):

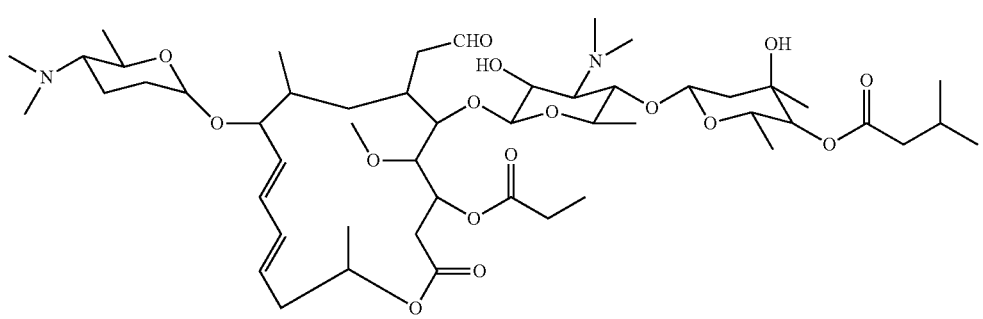

The specific optical rotation $[\alpha]_D$ is (−) −49°~−51° (C=0.02 g/ml, CHCl₃, 25□, λ=589.3 nm); and the melting point is 116□~118□;

The present invention relates to a preparation of the levoisovalerylspiramycin I, wherein: the preparation comprises levoisovalerylspiramycin I, pharmaceutical salt of isovalerylspiramycin I, isovalerylspiramycin I and pharmaceutically acceptable adjuvant, or pharmaceutical salt of isovalerylspiramycin I and pharmaceutically acceptable adjuvant, wherein the purity of isovalerylspiramycin I is above 90 wt %, preferably, more than 95 wt %, and further preferably, more than 98 wt %;

The present invention relates to a preparation of the levoisovalerylspiramycin II, wherein: the preparation comprises isovalerylspiramycin II, pharmaceutical salt of isovalerylspiramycin II, isovalerylspiramycin II and pharmaceutically acceptable adjuvant, or pharmaceutical salt of isovalerylspiramycin II and pharmaceutically acceptable adjuvant, wherein the purity of isovalerylspiramycin II is above 90 wt %, preferably, more than 95 wt %, and further preferably, more than 98 wt %;

The present invention relates to a preparation of the levoisovalerylspiramycin III, wherein: the preparation comprises isovalerylspiramycin III, pharmaceutical salt of isovalerylspiramycin III, isovalerylspiramycin III and pharmaceutically acceptable adjuvant, or pharmaceutical salt of isovalerylspiramycin III and pharmaceutically acceptable adjuvant, wherein the purity of isovalerylspiramycin III is above 90 wt %, preferably, more than 95 wt %, and further preferably, more than 98 wt %.

A first preferred technical scheme of the present invention: the preparation of the present invention is liquid, solid, semisolid, or gas ones, wherein, the liquid preparation comprises injection, infusion solution, solution, mixture, sirup, tincture, colloid, aromatic water, glycerite, colloid solution, mucilage, suspension, or emulsion; the solid preparation comprises power injection, lyophilized powder injection, tablet, capsula, powder, granula, pill, sublimed preparation, or membrane; the semisolid preparation comprises ointment, plaster, suppository, extract, or gel; and the gas preparation comprises aerosol or spray; preferably, solution for injection, powder for injection or lyophilized powder for injection.

A second preferred technical scheme of the present invention: the preparation of the present invention containing levoisovalerylspiramycin I (unit dose) 10~1500 mg, preferably, 50~1000 mg, further preferably, 100~500 mg; the preparation of the present invention containing levoisovalerylspiramycin II (unit dose) 10~1500 mg, preferably, 50~1000 mg, further preferably, 100~500 mg; the preparation of the present invention containing levoisovalerylspiramycin III (unit dose) 10~1500 mg, preferably, 50~1000 mg, further preferably, 100~500 mg.

A third preferred technical scheme of the present invention: the weight percentage of levoisovalerylspiramycin I in the preparation is 10~95%, preferably, 50~95%, and further preferably, 75~95%; the weight percentage of levoisovalerylspiramycin II in the preparation is 10~95%, preferably, 50~95%, and further preferably, 75~95%; the weight percentage of levoisovalerylspiramycin III in the preparation is 10~95%, preferably, 50~95%, and further preferably, 75~95%.

The present invention also relates to a preparation containing levoisovalerylspiramycin I, levoisovalcrylspiramycin II or levoisovalerylspiramycin III respectively:

The preparation comprises solution for injection, powder for injection or lyophilized powder for injection prepared by isovalerylspiramycin I and at least one of citric acid, adipic acid and maleic acid; the preparation comprises solution for injection, powder for injection or lyophilized powder for injection prepared by isovalerylspiramycin II and at least one of citric acid, adipic acid and maleic acid; the preparation comprises solution for injection, powder for injection or lyophilized powder for injection prepared by isovalerylspiramycin III and at least one of citric acid, adipic acid and maleic acid.

Wherein, the molar ratio of levoisovalerylspiramycin I to citric acid is 1:0.8~4.2, the molar ratio of levoisovalerylspiramycin I to adipic acid is 1:0.8~1.2 and the molar ratio of levoisovalerylspiramycin I to maleic acid is 1:0.8~1.2; the molar ratio of levoisovalerylspiramycin II to citric acid is 1:0.8~1.2, the molar ratio of levoisovalerylspiramycin II to adipic acid is 1:0.8~1.2 and the molar ratio of levoisovalerylspiramycin II to maleic acid is 1:0.8~1.2; the molar ratio of levoisovalerylspiramycin III to citric acid is 1:0.8~1.2, the molar ratio of levoisovalerylspiramycin III to adipic acid is 1:0.8~1.2 and the molar ratio of levoisovalerylspiramycin III to maleic acid is 1:0.8~1.2.

The present invention relates to a method for preparing of levoisovalerylspiramycin I, II or III, including: preparing levocarrimycin and purifying levoisovalerylspiramycin I, II or III.

Wherein, the preparation process of levocarrimycin includes: culturing and biologically fermenting cloned fungal strains WSP-195 produced by spiramycin containing 4"-isovaleryl transferase gene, and extracting the fermentation liquor; fermentation proceeding on the condition of pH 6.0~9.0, preferably, 6.0~8.0, and further preferably, 6.0~7.5. The curves of pH variation with time show three continuous phases, wherein, the first phase satisfies formula $y_1=k_1x_1+6.0$, in which $0.0227 \leq k_1 \leq 0.1364$, $0<x_1 \leq 22$; the second phase satisfies formula $y_2=k_2x_2+b_2$, in which $-0.0735 \leq k_2<0$, $6.5<b_2 \leq 10.62$, $22 \leq x_2 \leq 56$; and the third phase satisfies formula $y_3=k_3x_3+b_3$, in which $0<k_3 \leq 0.0078$, $6.06 \leq b_3<6.5$, $56 \leq x_3 \leq 120$. In the present invention, by adjusting and optimizing the culture and fermentation conditions, especially by controlling the pH during the fermentation with pH regulator, the curves of pH variation with time show three continuous phases, and each phase satisfies certain formula respectively, thus levocarrimycin with optical activity is obtained. Further levoisovalerylspiramycin I, II or III is respectively obtained by separation.

Preferably, biological fermentation conditions in the present invention is: culturing the cloned fungal strains WSJ-195 produced by spiramycin containing 4"-isovaleryl transferase gene on an agarslantculture-medium containing 2% soybean cake meal, 1% glucose, 3% starch, 0.5% $CaCO_3$, 0.4% NaCl and 2% agar for 8~15 days under pH6.5~7.5 and temperature 28~38□, then inoculating to a seed medium containing 1.5% soybean cake meal, 3.0% starch, 0.4% NaCl, 0.5% $CaCO_3$, 0.3% fish peptone and 0.05% $KH_2PO_4$ and culturing for 40~80 hours under pH6.5~7.5 and temperature 25~30□, implanting to a fermentation medium containing 0.5% glucose, 6.0% starch, 0.5% yeast powder, 2.0% fish meal, 0.6% $NH_4NO_3$, 1.0% NaCl, 0.5% $CaCO_3$, 0.05% $KH_2PO_4$, 0.1% $MgSO_4$, 0.5% soybean oil and 0.02% defoamer and culturing for 72~120 hours under pH6.5~7.5, temperature 26~30□ and 0.1~20% inoculation amount, to obtain fermentation liquor.

The pH regulator is at least one selected from glucose, citric acid, hydrochloric acid, acetic acid, ammonia, sodium hydroxide, and potassium hydroxide.

Preferably, the extraction process of biological fermentation liquor in the present invention is: proceeding the fermentation liquor with aluminum sulfate to obtain filtrate, regulating the pH of filtrate to 8.5~9.0, using butyl acetate for extraction, cleaning butyl acetate extract with non-saline and 1% $NaH_2PO_4$, then using pH2.0~2.5 water for extraction to obtain aqueous extract, regulating the pH of aqueous extract to 4.5~5.5, volatilizing and eliminating residual butyl acetate to obtain water extract, filtering the water extract, regulating the pH of filtrate to pH8.5~9.0, precipitating the filtrate and washing with purified water to obtain the wet product, and drying it to obtain levocarrimycin.

Wherein, at least one of hydrochloric acid, acetic acid, citric acid, sodium hydroxide, potassium hydroxide, sodium bicarbonate and sodium carbonate is adopted to regulate pH value.

Wherein, the purification process of levoisovalerylspiramycin I, II or III includes: purifying the levocarrimycin sample with chromatograph method, performing gradient elution and separating the component target peak of levoisovalerylspiramycin I, II or III via ODS chromatographic column in acetonitrile and ammonium acetate buffer solution.

Preferably, during the purification of levoisovalerylspiramycin I, II or III, recording the UV spectrum diagram of levoisovalerylspiramycin I, II or III through preparative high performance liquid chromatography and UV detection, and collecting levoisovalerylspiramycin I sample based on retention time 44.759 min, levoisovalerylspiramycin II sample based on retention time 43.34 min min, and levoisovalerylspiramycin III sample based on retention time 48.009 min.

Further preferably, during the purification of levoisovalerylspiramycin I, II or III, eliminating acetonitrile in the collected levoisovalerylspiramycin I, II or III respectively with rotary evaporation method, then using ethyl acetate for extraction, and eliminating the ethyl acetate in the extract by evaporation to obtain paste sample; re-dissolving the sample obtained with petroleum ether, eliminating the petroleum ether by evaporation to respectively obtain the white power of levoisovalerylspiramycin I, II or III.

Wherein, the mobile phase is a mixed solvent of acetonitrile A and 150 mM ammonium acetate solution with pH 8.5.

The conditions required for purifying levoisovalerylspiramycin I, II or III: linear gradient: 0~60 minutes, A being 25%~65%, and 61~90 minutes, A being 65%~90%;

Flow velocity: 260 mL/min;

Sample size: 10 mL;

Sample concentration: 0.5 g/mL;

Measurement wavelength: 231 nm;

Way of collecting: collection via UV triggering.

The present invention also relates to crystalline compound of levoisovalerylspiramycin I, the X-ray powder diffraction of which measured by Cu-Ka ray has characteristic peaks at $2\theta=7.6°$, 8.0°, 10.0°, 11.4°, 16.4°, 17.0°, 17.5°, 17.9°, 19.5°, 22.7°, 23.7° and 24.4°. The X-ray power diffraction diagram is shown in FIG. 5.

The method for preparing the crystalline compound of levoisovalerylspiramycin I is: dissolving solid levoisovalerylspiramycin I compound in a mixed solvent of ethyl acetate, absolute ethyl alcohol and anhydrous acetone, adding pure water and stirring the mixture simultaneously, cooling to 5° C.~15° C. after adding pure water, continuing stirring when cooling, then obtaining crystalline compound of levoisovalerylspiramycin I.

Wherein, a first preferable technical scheme of the method for preparing the crystalline compound of levoisovalerylspiramycin I is: the volume of added pure water being 2~9 times of the total volume of ethyl acetate, absolute ethyl alcohol and anhydrous acetone, preferably, 2.5~7.5 times, and the adding velocity of water is 4~10 ml/minute, preferably, 6~8 ml/minute.

A second preferable technical scheme of the method for preparing said the crystalline compound of levoisovalerylspiramycin I is: the volume ratio of ethyl acetate, absolute ethyl alcohol and anhydrous acetone in the mixed solvent being 1:0.1~10:0.5~1, preferably, 1:2~8:0.8~1.

A third preferable technical scheme of the method for preparing the crystalline compound of levoisovalerylspiramycin I is: the stirring rate of added pure water being 30~60 r/min, preferably, 45~60 r/min; the stirring rate after adding pure water being 10~30 r/min, preferably, 10~20 r/min.

A fourth preferable technical scheme of the method for preparing the crystalline compound of levoisovalerylspiramycin I is: the cooling rate after adding pure water being 1~3° C./hour, preferably, 1~1.5 □/hour.

The present invention also relates to crystalline compound of levoisovalerylspiramycin II, the X-ray powder diffraction of which measured by Cu-Ka ray has characteristic peaks at 2θ=10.0°, 11.6°, 16.4°, 17.3°, 19.1°, 21.2°, 22.1°, 22.7°, 26.4°, 26.9°, 27.5° and 31.5°. The X-ray power diffraction diagram is shown in FIG. 6.

The method for preparing the crystalline compound of levoisovalerylspiramycin II is: dissolving solid levoisovalerylspiramycin II compound in a mixed solvent of absolute methanol, absolute ethyl alcohol and anhydrous acetone, adding pure water and stirring the mixture simultaneously, cooling to 5□~15□ after adding pure water, continuing stirring when cooling, then obtaining crystalline compound of levoisovalerylspiramycin II.

Wherein, a first preferable technical scheme of the method for preparing the crystalline compound of levoisovalerylspiramycin II is: the volume of added pure water being 2~9 times of the total volume of absolute methanol, absolute ethyl alcohol and anhydrous acetone, preferably, 2.5~7.5 times, and the adding velocity of water being 4~10 ml/minute, preferably, 6~8 ml/minute.

A second preferable technical solution of preparation method of said crystalline compound of levoisovalerylspiramycin II is: the volume ratio of absolute methanol, absolute ethyl alcohol and anhydrous acetone in the mixed solvent being 1:0.1~10:0.5~1, preferably, 1:2~8:0.8~1.

A third preferable technical scheme of the method for preparing the crystalline compound of levoisovalerylspiramycin II is: the stirring rate of adding pure water being 30~60 r/min, preferably, 45~60 r/min; the stirring rate after adding pure water being 10~30 r/min, preferably, 10~20 r/min.

A fourth preferable technical scheme of the method for preparing the crystalline compound of levoisovalerylspiramycin II being: the cooling rate after adding pure water being 1~3 □/hour, preferably, 1~1.5 □/hour.

The present invention also relates to crystalline compound of levoisovalerylspiramycin III, the X-ray powder diffraction of which measured by Cu-Ka ray has characteristic peaks at 2θ=8.0°, 10.0°, 112°, 11.7°, 16.4°, 19.1°, 19.6°, 20.0°, 21.4°, 22.9°, 23.6° and 29.4°. The X-ray power diffraction diagram is shown in FIG. 7.

The method for preparing the crystalline compound of levoisovalerylspiramycin III is: dissolving solid levoisovalerylspiramycin III compound in a mixed solvent of absolute methanol, absolute ethyl alcohol and anhydrous acetone, adding pure water and stirring the mixture simultaneously, cooling to 5□~15□ after adding pure water, continuing stirring when cooling, then obtaining crystalline compound of levoisovalerylspiramycin III.

Wherein, a first preferable technical scheme of the method preparing the crystalline compound of levoisovalerylspiramycin III is: the volume of added pure water being 2~9 times of the total volume of absolute methanol, absolute ethyl alcohol and anhydrous acetone, preferably, 2.5~7.5 times, and the adding velocity of water being 4~10 ml/minute, preferably, 6~8 ml/minute.

A second preferable technical scheme of the method for preparing the crystalline compound of levoisovalerylspiramycin III is: the volume ratio of absolute methanol, absolute ethyl alcohol and anhydrous acetone in the mixed solvent being 1:0.1~10:0.5~1, preferably, 1:2~8:0.8~1.

A third preferable technical scheme of the method for preparing the crystalline compound of levoisovalerylspiramycin III is: the stirring rate of adding pure water being 30~60 r/min, preferably, 45~60 r/min; the stirring rate after adding pure water being 10~30 r/min, preferably, 10~20 r/min.

A fourth preferable technical scheme of the method for preparing the crystalline compound of levoisovalerylspiramycin III is: the cooling rate after adding pure water being 1~3 □/hour, preferably, 1~1.5 □/hour.

The molecules in different types of crystal cells are different in steric configuration, conformation and arrangement, thus the solubility is obviously different, resulting in a situation that the preparations have different digestion rates in human body, which directly affects the absorption, distribution, excretion and metabolism of the preparations in human body and finally leads to difference in clinical pharmaceutical effect due to different biological availability. Through comparison on effect between said crystal of levoisovalerylspiramycin I, II or III prepared in the present invention and levoisovalerylspiramycin I, II or III, it is found that the effect of crystal of the levoisovalerylspiramycin I, II or III prepared in the present invention is superior to that of levoisovalerylspiramycin I, II or III respectively.

The present invention also relates to a preparation of crystalline compound of levoisovalerylspiramycin I, which includes crystalline compound of isovalerylspiramycin I, pharmaceutical salt of crystalline compound of isovalerylspiramycin I, crystalline compound of isovalerylspiramycin I and pharmaceutically acceptable adjuvant, or pharmaceutical salt of crystalline compound of isovalerylspiramycin I and pharmaceutically acceptable adjuvant, wherein, the purity of crystalline compound of isovalerylspiramycin I is above 99 wt %;

The present invention also relates to a preparation of crystalline compound of levoisovalerylspiramycin II, which includes crystalline compound of isovalerylspiramycin II, pharmaceutical salt of crystalline compound of isovalerylspiramycin II, crystalline compound of isovalerylspiramycin II and pharmaceutically acceptable adjuvant, or pharmaceutical salt of crystalline compound of isovalerylspiramycin II and pharmaceutically acceptable adjuvant, wherein, the purity of crystalline compound of isovalerylspiramycin II is above 99 wt %;

The present invention also relates to a preparation of crystalline compound of levoisovalerylspiramycin III, which includes crystalline compound of isovalerylspiramycin III, pharmaceutical salt of crystalline compound of isovalerylspiramycin III, crystalline compound of isovalerylspiramycin III and pharmaceutically acceptable adjuvant, or pharmaceutical salt of crystalline compound of isovalerylspiramycin III and pharmaceutically acceptable adjuvant, wherein, the purity of crystalline compound of isovalerylspiramycin III is above 99 wt %.

The present invention also relates to a use of isovalerylspiramycin I, crystalline compound and the preparation thereof in preparing a drug for treating and/or preventing anti-infectious diseases; the present invention also relates to a use of isovalerylspiramycin II, crystalline compound and the preparation thereof in preparing a drug for treating and/or preventing anti-infectious diseases; the present invention also relates to a use of isovalerylspiramycin III, crystalline compound and the preparation thereof in preparing a drug for treating and/or preventing anti-infectious diseases. The infectious diseases include diseases caused by gram-positive bacterium, *staphylococcus aureus, streptococcus pneumoniae, mycoplasma pneumoniae, chlamydia pneumoniae, ureaplasma urealyticum, Chlamydia trachomatis, pyogenic streptococcus, Micrococcus catarrhalis, gonococcus, bacillus influenzae, legionella* or *anaerobe*.

The present invention also relates to a use of isovalerylspiramycin I, crystalline compound and the preparation thereof in preparing an antibiotic drug; the present invention also relates to a use of isovalerylspiramycin II, crystalline compound and the preparation thereof in preparing an antibiotic drug; the present invention also relates to a use of isovalerylspiramycin III, crystalline compound and the preparation thereof in preparing an antibiotic drug. The bacteria herein include *streptococcus pneumoniae*, Group A *streptococcus, pyogenic streptococcus, enterococcus, staphylococcus aureus, S. epidermids, Catarrhal coccus, gonococcus, bacillus influenzae, escherichia coli*, enterotoxigenic *escherichia coli*, enteropathogenic *escherichia coli*, enteroinvasive *Escherichia coli, Pseudomonas aeruginosa, Klebsiella pneumoniae, bacillus proteus vulgaris*, typhoid *bacillus, acinetobacter, citrobacter, Serratia marcescens, S. Sonnei, Sh. flexneri, Tritirachium album; legionella* like *legionella pneumophila, legionella gormanii, legionella bozemanii, legionella dumoffii, legionella jordanis*, and *legionella micdadei*; anaerobe like *bacteroides fragilis, B. thetaiotaomicron, B. vulgatus, B. distasonis, B. prevotella, Prevotella asaccharolyticus, Prevotella oralis, Fusobacteriumnu cleatum, Fusobacterium russll, bifidobacteria, lactobacillus, peptostreptococcus, propionibacterium acnes, clostridium perfringens*, and yeast-like fungus.

The following is a further detailed description of the present invention.

The present invention relates to levoisovalerylspiramycin I, which is obtained through adjustment and optimization of the culture and fermentation conditions and strict control of the solution pH value.

The present invention relates to levoisovalerylspiramycin II, which is obtained through adjustment and optimization of the culture and fermentation conditions and strict control of the solution pH value.

The present invention relates to levoisovalerylspiramycin III, which is obtained through adjustment and optimization of the culture and fermentation conditions and strict control of the solution pH value.

The levoisovalerylspiramycin I, II or III of the present invention has a good antibacterial activity, which adds a new variety applicable for injection to antibiotic drugs and presents a new solution to the technical problem of the present antibiotic resistance.

Wherein, the measuring method of specific rotation of levoisovalerylspiramycin I, II or III in the present invention is: precisely weighting this product, adding chloroform for dissolution, diluting it into a solution with 20 mg/ml, Adopting line D of Sodium spectrum (589.3 nm) to measure the optical activity at a measuring length of 1 dm and a temperature of 25□, and using a polarimeter which has a reading to 0.0001° and has been calibrated beforehand.

The measuring method of melting point of levoisovalerylspiramycin I, II or III in the present invention is: putting dry levoisovalerylspiramycin I, II or III at a proper amount to a capillary tube used for melting point measuring, measuring the melting point, repeating the measuring for 3 times to get an average value.

The present invention also relates to the preparation containing levoisovalerylspiramycin I, II or III, which includes levoisovalerylspiramycin I and pharmaceutically acceptable carrier and/or adjuvant, wherein the purity of levoisovalerylspiramycin I, II or III is more than 90 wt %, preferably, more than 95 wt %, and further preferably, more than 98 wt %.

The preparation containing levoisovalerylspiramycin I, II or III or its crystalline compound prefers solution for injection, powder for injection and lyophilized powder for injection. The single-component preparation containing levoisovalerylspiramycin I, II or III is made into solution for injection or powder for injection, so that the preparation of levoisovalerylspiramycin I, II or III in the present invention can be better absorbed by human body to take effect in anti-infection.

The preparation containing levoisovalerylspiramycin I in the present invention includes the following unit dose: levoisovalerylspiramycin I 10~1500 mg, preferably, 50~1000 mg, and further preferably, 100~500 mg;

The preparation containing levoisovalerylspiramycin II in the present invention includes the following unit dose: levoisovalerylspiramycin II 10~1500 mg, preferably, 50~1000 mg, and further preferably, 100~500 mg;

The preparation containing levoisovalerylspiramycin III in the present invention includes the following unit dose: levoisovalerylspiramycin III 10~1500 mg, preferably, 50~1000 mg, and further preferably, 100~500 mg.

The preparation containing crystalline compound of levoisovalerylspiramycin I in the present invention includes the following unit dose: crystalline compound of levoisovalerylspiramycin I 10~1500 mg, preferably, 50~1000 mg, and further preferably, 100~500 mg;

The preparation containing crystalline compound of levoisovalerylspiramycin II in the present invention includes the following unit dose: crystalline compound of levoisovalerylspiramycin II 10~1500 mg, preferably, 50~1000 mg, and further preferably, 100~500 mg;

The preparation containing crystalline compound of levoisovalerylspiramycin III in the present invention includes the following unit dose: crystalline compound of levoisovalerylspiramycin III 10~1500 mg, preferably, 50~1000 mg, and further preferably, 100~500 mg.

The weight percentage of levoisovalerylspiramycin I in the preparation containing levoisovalerylspiramycin I in the present invention is 10~90%, preferably, 50~90%, and further preferably, 75%~90%;

The weight percentage of levoisovalerylspiramycin II in the preparation containing levoisovalerylspiramycin II in the present invention is 10~90%, preferably, 50~90%, and further preferably, 75%~90%;

The weight percentage of levoisovalerylspiramycin III in the preparation containing levoisovalerylspiramycin III in the present invention is 10~90%, preferably, 50~90%, and further preferably, 75%~90%.

The weight percentage of the crystalline compound of levoisovalerylspiramycin I in the preparation containing levoisovalerylspiramycin I compound crystalline compound of the present invention is 10~90%, preferably 50~90%, further preferably 75%~90%;

The weight percentage of the crystalline compound of levoisovalerylspiramycin II in the preparation containing crystalline compound of levoisovalerylspiramycin II in the present invention is 10~90%, preferably, 50~90%, and further preferably, 75%~90%;

The weight percentage of the crystalline compound of levoisovalerylspiramycin III in the preparation containing levoisovalerylspiramycin III compound crystal in the present invention is 10~90%, preferably, 50~90%, and further preferably, 75%~90%.

The oral preparation in the present invention can contain common excipient, such as adhesive, filler, diluents, tablet pressing agent, lubricating agent, disintegrant, colorant, condiment or humectant, and the tablet can be coated if necessary. Wherein, applicable filler includes cellulose, mannite, lactos and other similar fillers; applicable disintegration agent includes starch, polyvinylpyrrolidone and starch derivatives like sodium starch glycollate; applicable disintegrant includes, for example, magnesium stearate; and applicable pharmaceutically acceptable humectant includes lauryl sodium sulfate.

The oral solid preparation in the present invention can be prepared through common methods such as blending, filling and pressing.

The oral liquid preparation of the present invention can be in a form of, for example, water-based or oil-based suspension, solution, emulsion, syrups or elixir, or it can be a drying product that can be duplicated by water or other applicable carrier before use. This liquid preparation can contain conventional additives, such as suspending agent like sorbitol, syrup, methyl cellulose, gelatin, hydroxyethyl cellulose, carboxymethyl cellulose, aluminum stearate gel or edible hydrogenate fat, and emulsifier, like lecithin, sorbitan oleate or Arabic gum; non-aqueous carriers (which may include edible oil), such as almond oil, fractional coconut oil and oil ester like glycerol, propylene glycol or ethanol; preservatives, such as parabens or Propyl 4-hydroxybenzoate or sorbic acid, in addition, can contain conventional flavoring agent or colorant if necessary.

The injection of the present invention can contain any common medicinal carriers and/or excipient, stabilizing agent, antioxidant, complexing agent, or medicinal preservatives, buffer agent or local anesthetics and the like. The injection is prepared with conventional preparation method.

The pharmaceutically acceptable carriers in the preparation of the present invention are selected from: mannitol, sorbitol, sodium pyrosulfite, sodium bisulfite, sodium thiosulfate, crysteine hydrochloride, mercaptoacetic acid, methionine, vitamin C, EDTA disodium, EDTA sodium calcium, monobasic carbonate, acetate, phosphate or its water solution, muriatic acid, acetic acid, sulfuric acid, phosphoric acid, amino acid, sodium chloride, potassium chloride, sodium lactate, xylitol, maltose, glucose, fructose, dextran, glycine, starch, sugar, lactose, mannitol, silicon derivatives, cellulose and its derivatives, alginate, gelatin, polyvinylpyrrolidone, glycerol, tween-80, agar, calcium carbonate, calcium bicarbonate, surfactant, polyethylene glycol, cyclodextrin, β-cyclodextrin, materials of phospholipids, kaolin, talcum powder, calcium stearate, magnesium stearate, etc.

The usage and dosage of the preparation of the present invention is based on the practical situations of the patients. It can be taken orally or injected for 1~3 times with 1~20 doses in each time a day.

The beneficial effects of the present invention are:

(1) levoisovalerylspiramycin I, II or III of the present invention has a good antibacterial performance. According to modern pharmacological studies, due to a difference in the stereoselectivity of drug enantiomers, the affinity of a drug to each receptor is also different, thus resulting in great differences in pharmacologic action. Therefore, levoisovalerylspiramycin I, II or III of the present invention has a strong pharmacologic activity;

(2) the molecules in different types of crystal cells of are different in steric configuration, conformation and arrangement, thus the solubility is obviously different, resulting in a situation that the preparations have different digestion rates in human body, which directly affects the absorption, distribution, excretion and metabolism of the preparations in human body and finally leads to difference in clinical pharmaceutical effect due to different biological availability. Through comparison on effect between crystalline compound of levoisovalerylspiramycin I, II or III prepared in the invention and levoisovalerylspiramycin I, II or III, it is found that the effect of crystal of levoisovalerylspiramycin I, II or III prepared in the present invention is superior to that of levoisovalerylspiramycin I, II or III respectively.

(3) the injection containing single component of levoisovalerylspiramycin I, II or III, or the injection containing single component of the crystalline compound of levoisovalerylspiramycin I, II or III provides a possibility of a dosage form, which can take effect quickly and be easily accepted for critically ill patients or those who can't take drugs orally;

(4) the preparation containing single component of levoisovalerylspiramycin I, II or III, or the preparation containing single component of crystalline compound of levoisovalerylspiramycin I, II or III of the present invention have a stable production process, and an easily controlled quality standard, apply to large-scale industrial production.

The following embodiments only explain and interpret the present invention, but can't have any limit to the content of the present invention.

Embodiments

Embodiment 1 Separation and Preparation of Levoisovalerylspiramycin I, II and III (1) biological fermentation: culturing the cloned fungal strains WSJ-195 produced by spiramycin containing 4"-isovaleryl transferase gene on an agarslantculture-medium containing 2% soybean cake meal, 1% glucose, 3% starch, 0.5% $CaCO_3$, 0.4% NaCl and 2% agar for 8~15 days under pH6.5~7.5 and temperature 28~38□, then inoculating to a seed medium containing 1.5% soybean cake meal, 3.0% starch, 0.4% NaCl, 0.5% $CaCO_3$, 0.3% fish peptone and 0.05% $KH_2PO_4$ to be cultured for 40~80 hours under pH6.5~7.5 and temperature 25~30□, implanting to a fermentation medium containing 0.5% glucose, 6.0% starch, 0.5% yeast powder, 2.0% fish meal, 0.6% $NH_4NO_3$, 1.0% NaCl, 0.5% $CaCO_3$, 0.05% $KH_2PO4$, 0.1% $MgSO_4$, 0.5% soybean oil and 0.02% defoamer to be cultured for 72~120 hours under pH6.5~7.5, temperature 26~30□, and 0.1~20% inoculation amount, then obtaining fermentation liquor.

Figure 1:
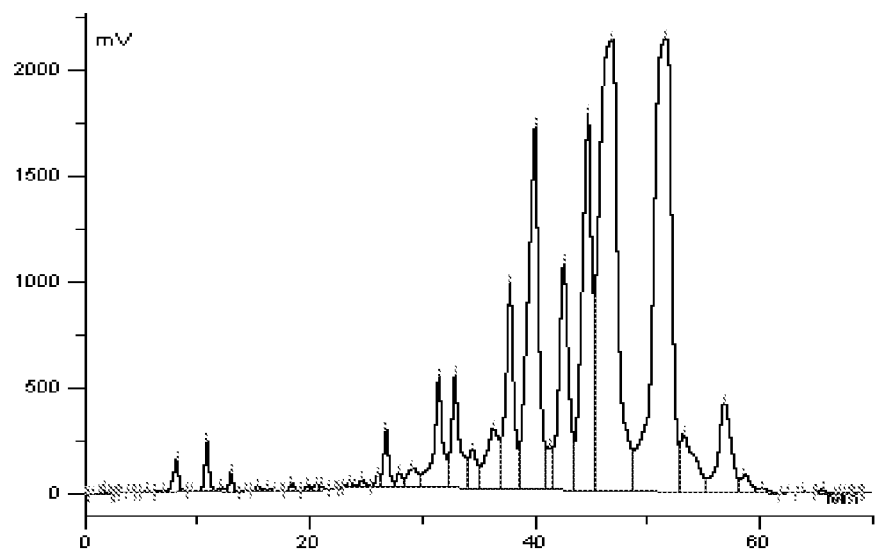
FIG. 1 shows the chromatogram collected by ultraviolet triggering of levoisovalerylspiramycin I, II or III in embodiment 1.
Figure 2:
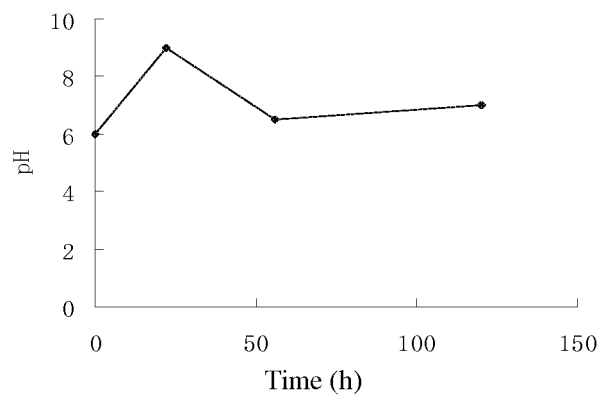
FIG. 2 shows the variation curve of pH value with time of the fermentation process in embodiment 1 of the present invention.

Wherein, strictly control the pH value of solution through adjustment and optimization of culture and fermentation conditions; fermentation proceeds for 120 h on the condition of pH 6.0~9.0, and the curves of pH variation with time show three continuous phases, wherein, the first phase satisfies formula $y_1=0.1364x_1+6.0$, in which $0<x_1 \leq 22$; the second phase satisfies formula $y_2=-0.0735x_2+10.64$, in which $22 \leq x_2 \leq 56$; and the third phase satisfies formula $y_3=0.0078x_3+6.06$, in which $56 \leq x_3 \leq 120$. FIG. 2 shows the curves. Fermentation liquor is obtained.

(2) extraction of biological fermentation liquor: proceeding the fermentation liquor obtained in step (1) with aluminum sulfate to obtain filtrate, regulating the pH to 8.5, using butyl acetate for extraction, cleaning butyl acetate extract respectively with non-saline and 1% $NaH_2PO_4$, then using pH2.0 water for extraction to obtain aqueous extract, regulating the pH to 4.5, volatilizing and eliminating the residual butyl acetate to obtain water extract, filtering, and regulating the pH to pH8.5, precipitating the filtrate and washing with purified water to obtain the wet product, and drying it to obtain levocanimycin.

(3) purification of levoisovalerylspiramycin I, II and III: purifying the preliminarily separated sample with preparative liquid chromatography, gradually eluting via ODS chromatographic column in acetonitrile and ammonium acetate buffer solution, and recording the separation ultraviolet spectrum diagram via UV detection, and collecting the component target peak of levoisovalerylspiramycin I, II or III.

Chromatographic column: ODS-prepared chromatographic column;

Mobile phase: acetonitrile (A), 100 mM ammonium acetate aqueous solution (B);

Gradient condition: linear gradient for 0~60 minutes, A being 25%~65%, and 61~90 minutes, A being 65%~90%;

Flow velocity: 260 mL/min;

Sample size: 10 mL;

Sample concentration: 0.5 g/mL;

Measurement wavelength: 231 nm;

Way of collecting: collection via UV triggering.

Collecting levoisovalerylspiramycin I sample based on retention time 44.759 min, levoisovalerylspiramycin II sample based on retention time 43.34 min, and levoisovalerylspiramycin III sample based on retention time 48.009 min.

Eliminating acetonitrile in the collected levoisovalerylspiramycin I, II or III respectively with rotary evaporation method, then using doubled ethyl acetate for extraction, eliminating the ethyl acetate in the extract with rotary evaporate, and obtaining paste sample; re-dissolving the obtained sample in petroleum ether, eliminating the petroleum ether with rotary evaporation to respectively obtain the white power of levoisovalerylspiramycin I, II or III.

Figure 3:
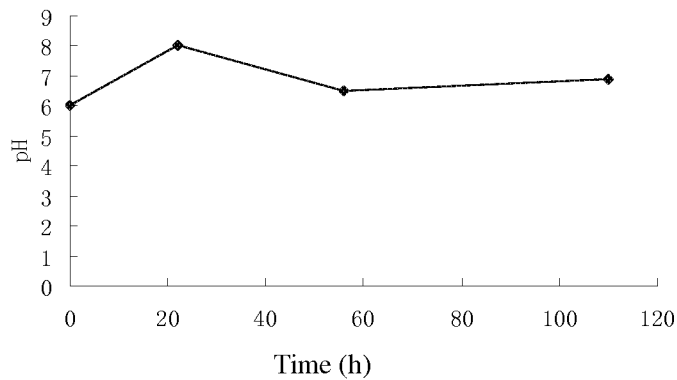
FIG. 3 shows the variation curve of pH value with time of the fermentation process in embodiment 2 of the present invention.

Embodiment 2 Separation and Preparation of Levoisovalerylspiramycin I, II and III (1) biological fermentation: culturing the cloned fungal strains WSJ-195 produced by spiramycin containing 4"-isovaleryl transferase gene on an agarslant culture-medium containing 2% soybean cake meal, 1% glucose, 3% starch, 0.5% $CaCO_3$, 0.4% NaCl and 2% agar for 12 days under pH 7.2 and temperature 32□, then inoculating to a seed medium containing 1.5% soybean cake meal, 3.0% starch, 0.4% NaCl, 0.5% $CaCO_3$, 0.3% fish peptone and 0.05% $KH_2PO_4$ and culturing for 70 hours under pH7.2 and temperature 27□, implanting to a fermentation medium containing 0.5% glucose, 6.0% starch, 0.5% yeast powder, 2.0% fish meal, 0.6% $NH_4NO_3$, 1.0% NaCl, 0.5% $CaCO_3$, 0.05% $KH_2PO_4$, 0.1% $MgSO_4$, 0.5% soybean oil and 0.02% defoamer, and culturing for 100 hours under pH6.0~9.0, temperature 26□ and 12% inoculation amount, then obtaining fermentation liquor. Fermentation proceeds for 110 h under pH 6.0~8.0, and the curves of pH variation with time show three continuous phases, wherein, the first phase satisfies formula $y_1=0.0909x_1+6.4$, in which $0<x_1<22$; the second phase satisfies formula $y_2=-0.0441x_2+7.8$, in which $22<x_2<56$; and the third phase satisfies formula $y_3=0.0078x_3+6.06$, in which $56 \leq x_3 \leq 110$. FIG. 3 shows the curves. Fermentation liquor is obtained. See FIG. 3 for specific control curves.

(2) extraction of biological fermentation liquor: proceeding the fermentation liquor in step (1) with aluminum sulfate to obtain filtrate, regulating the pH to 8.6, using butyl acetate for extraction, cleaning butyl acetate extract respectively with non-saline and 1% $NaH_2PO_4$, then using water with pH 2.3 for extraction to obtain aqueous extract, regulating the pH to 5.0, volatilizing and eliminating the residual butyl acetate to obtain water extract, filtering, and regulating the pH to pH8.6, precipitating the filtrate, and washing with purified water to obtain the wet product, and drying it to obtain levocarrimycin.

(3) purification of levoisovalerylspiramycin I, II or III: purifying the preliminarily separated sample via with preparative liquid chromatography, gradually eluting via ODS preparative chromatographic column in acetonitrile and ammonium acetate buffer solution, recording the separation ultraviolet spectrum diagram via UV detection, and collecting the component target peak of levoisovalerylspiramycin I, II or III.

Chromatographic column: ODS preparative chromatographic column;

Mobile phase: acetonitrile (A), 100 mM ammonium acetate aqueous solution (B);

Gradient condition: linear gradient for 0~60 minutes, A being 25%~65%, and 61~90 minutes, A being 65%~90%;

Flow velocity: 260 mL/min;

Sample size: 10 mL;

Sample concentration: 0.5 g/mL;

Measurement wavelength: 231 nm;

Way of collecting: collection via UV triggering.

Collecting levoisovalerylspiramycin I sample based on retention time 44.759 min, levoisovalerylspiramycin II sample based on retention time 43.34 min, and levoisovalerylspiramycin III sample based on retention time 48.009 min;

Eliminating acetonitrile in the collected levoisovalerylspiramycin I, II or III respectively with rotary evaporation method, then using doubled ethyl acetate for extraction, eliminating the ethyl acetate in the extract with rotary evaporation, and obtaining paste sample; re-dissolving the obtained sample in petroleum ether, eliminating the petroleum ether with rotary evaporation to respectively obtain the white power of levoisovalerylspiramycin I, II or III.

Figure 4:
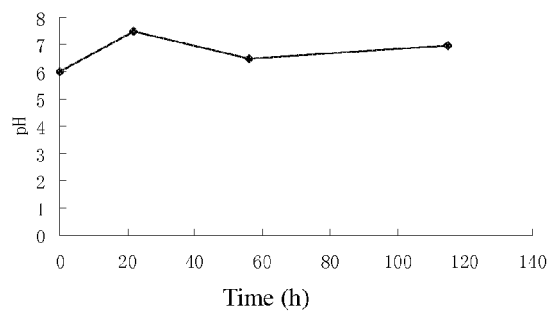
FIG. 4 shows the variation curve of pH value with time of the fermentation process in embodiment 3 of the present invention.

Embodiment 3 Separation and Preparation of Levoisovalerylspiramycin I, II and III (1) culture and fermentation: culturing the cloned fungal strains WSJ-195 produced by spiramycin containing 4"-isovaleryl transferase gene on an agarslant culture-medium, inoculating to a seed medium to be cultured, and then inoculating to fermentation medium, and the fermentation proceeding for 115 h under pH 6.0~7.5 which is controlled by glucose and citric acid during the fermentation process. The curves of pH variation with time show three continuous phases, wherein, the first phase satisfies formula $y_1=0.0682x_1+6.0$, in which $0<x_1\leq22$; the second phase satisfies formula $y_2=-0.0294x_2+8.147$, in which $22\leq x_2\leq56$; and the third phase satisfies formula $y_3=0.0078x_3+6.06$, in which $56<x_3<115$. FIG. 4 shows the curves. Fermentation liquor is obtained.

(2) extraction of biological fermentation liquor: proceeding the fermentation liquor in step (1) with aluminum sulfate to obtain filtrate, regulating the pH to 8.6, using butyl acetate for extraction, cleaning butyl acetate extract respectively with non-saline and 1% $NaH_2PO_4$, then using water with pH 2.3 for extraction to obtain aqueous extract, regulating the pH to 5.0, volatilizing and eliminating the residual butyl acetate to obtain water extract, filtering, and regulating the pH to pH 8.6, precipitating the filtrate, and washing with purified water to obtain the wet product, and drying it to obtain levocarrimycin.

(3) purification of levoisovalerylspiramycin I, II or III: purifying the preliminarily separated sample with preparative liquid chromatography, gradually eluting via ODS preparative chromatographic column in acetonitrile and ammonium acetate buffer solution, recording the separation ultraviolet spectrum diagram via UV detection, and collecting the component target peak of levoisovalerylspiramycin I, II or III.

Chromatographic column: adopt ODS preparative chromatographic column;

Mobile phase: acetonitrile (A), 100 mM ammonium acetate aqueous solution (B);

Gradient condition: linear gradient for 0~60 minutes, A being 25%~65%, and 61~90 minutes, A being 65%~90%;

Flow velocity: 260 mL/min;
Sample size: 10 mL;
Sample concentration: 0.5 g/mL;
Detection wavelength: 231 nm;
Collection method: collection via UV trigger;

Collecting levoisovalerylspiramycin I sample based on retention time 44.759 min, levoisovalerylspiramycin II sample based on retention time 43.34 min, and levoisovalerylspiramycin III sample based on retention time 48.009 min;

Eliminating acetonitrile in the collected levoisovalerylspiramycin I, II or III respectively with rotary evaporation method, then using doubled ethyl acetate for extraction, eliminating the ethyl acetate in the extract with rotary evaporate to obtain paste sample; re-dissolving the obtained sample in petroleum ether, eliminating the petroleum ether with rotary evaporation to respectively obtain the white power of levoisovalerylspiramycin I, II or III.

Embodiment 4 Preparation of Levoisovalerylspiramycin I Solution for Injection (1) mixing uniformly 100 mg isovalerylspiramycin I and adipic acid with equal mole, and dissolving into 1~5 ml distilled water to obtain light yellow and transparent solution, with a pH 4.6~5.6.

(2) adding activated carbon which is 0.1% of the solution in volume into the solution prepared in step (1), and filtering the solution;

(3) filling, sealing, sterilizing, inspecting and packing under aseptic condition.

Embodiment 5 Preparation of Isovalerylspiramycin I Solution for Injection (1) mixing uniformly 100 mg isovalerylspiramycin I and citric acid with equal mole, and dissolving into 1~5 ml distilled water to obtain light yellow and transparent solution, with a pH 4.6~5.6.

(2) adding activated carbon which is 0.1% of the solution in volume into the solution prepared in step (1), and filtering the solution;

(3) filling, sealing, sterilizing, inspecting and packing under aseptic condition.

Embodiment 6 Preparation of Isovalerylspiramycin I Solution for Injection (1) mixing uniformly 100 mg isovalerylspiramycin I and maleic acid with equal mole, and dissolving into 1~5 ml distilled water to obtain light yellow and transparent solution, with a pH 4.6~5.6.

(2) adding activated carbon which is 0.1% of the solution in volume to solution prepared in step (1), and filtering the solution;

(3) filling, sealing, sterilizing, inspecting and packing under aseptic condition.

Embodiment 7 Preparation of Levoisovalerylspiramycin I Power for Injection (1) mixing uniformly 100 mg levoisovalerylspiramycin I and citric acid with equal mole, and dissolving into 1~5 ml distilled water to obtain light yellow and transparent solution, with a pH 4.6~5.6.

(2) adding activated carbon which is 0.1% of the solution in volume into the solution prepared in step (1), and filtering the solution;

(3) adding 30~150 mg mannitol as lyophilization proppant; quickly freezing for 9 h under a low temperature, and drying to obtain light yellow loose lump, then capping, inspecting and packing under aseptic condition.

Embodiment 8 Preparation of Levoisovalerylspiramycin I Power for Injection (1) mixing uniformly 100 mg levoisovalerylspiramycin I and maleic acid with equal mole, and dissolving into 1~5 ml distilled water to obtain light yellow and transparent solution, with a pH 4.6~5.6.

(2) adding activated carbon which is 0.1% of the solution in volume to the solution prepared in step (1), and filtering the solution;

(3) adding 30~150 mg mannitol as lyophilization proppant; quickly freezing for 9 h under a low temperature, and drying to obtain light yellow loose lump, then capping, inspecting and packing under aseptic condition.

Embodiment 9 Preparation of Levoisovalerylspiramycin I Power for Injection (1) mixing uniformly 100 mg levoisovalerylspiramycin I and citric acid with equal mole, and dissolving into 1~5 ml distilled water to obtain light yellow and transparent solution, with a pH 4.6~5.6.

(2) adding activated carbon which is 0.1% of the solution in volume into the solution prepared in step (1), and filtering the solution;

(3) adding 30~150 mg mannitol as lyophilization proppant; quickly freezing for 9 h under a low temperature, and drying to obtain light yellow loose lump, then capping, inspecting and packing under aseptic condition.

Embodiment 10 Levoisovalerylspiramycin I Tablets (Calculated in 1000 Tablets)

| | |
|---|---|
| Formula: Levoisovalerylspiramycin I | 100 g |
| Low-substituted hydroxypropyl cellulose (5%) | 9.25 g |
| Sodium carboxymethyl starch (3%) | 5.55 g |
| Magnesium stearate (1%) | 1.85 g |
| Starch | Total weight—weight of other adjuvants |
| Total weight | 185 g |

Preparation process: weighing appropriate starch and diluting to 15% concentration, heating it until paste to prepare adhesive; sieving carrimycin as active component, adjuvants containing starch, low-substituted hydroxypropyl cellulose, sodium carboxymethyl starch and magnesium stearate respectively with a 100-mesh sieve, and weighing the active component and adjuvants required according to the formula; fully mixing levoisovalerylspiramycin I, starch and low-substituted hydroxypropyl cellulose, using 15% starch paste to prepare soft material, making the soft material into granules with 14-mesh sieve, drying under 50~60□ until water content controlled at 3-5%; sorting the granules with 14-mesh sieve, adding sodium carboxymethyl starch and magnesium stearate for mixing, determining the content of granules; calculating the weight of each tablet according to the content of granules; pressing the tablets (Φ9 mm dimple punch), detecting the tablet weight difference, and then packing the qualified tablets after detection.

Embodiment 11 Levoisovalerylspiramycin Capsules (Calculated in 1000 Capsules)

| Formula: Levoisovalerylspiramycin I raw powder | 100 g |
|---|---|
| Starch (for pharmaceutical use) | 108-levoisovalerylspiramycin I raw powder weight |
| Pharmaceutical No. 3 capsule | 100 granules |
| Liquid paraffin | 5 ml |

Preparation process: weighing levoisovalerylspiramycin I as active ingredient, adjuvant starch (for pharmaceutical use) respectively according to the formula and then putting them into a mixer to fully mixing for 1.5-2 hours; the data of sample content detected should be basically consistent with the theoretical data (about 0.105 g for each capsule). Filling the conforming pharmaceutical No. 3 capsule and mixed material to be filled into the filler according to the operation requirements of full-automatic capsule machine; detecting difference of the filled capsules (within ±10%, <0.3 g) and dissolution rate, put the conforming capsules into the glazing machine and adding liquid paraffin for glazing for 15-20 minutes, and then taking out for detection of finished product packing box.

Embodiment 12 Levoisovalerylspiramycin I Sugar-Coated Tablets (Calculated in 1000 Tablets)

Formula: the same as Embodiment 10

Preparation process: according to the operation method given in Embodiment 12, putting the conforming tablet cores into a pot for coating sugar and the prepared syrup (concentration 65%-70%) being slowly putting into the pot, then rising the temperature to about 40□, adding appropriate talcum powder, blowing repeatedly to dry for 25-30 minutes until subcoating being plain, then coating for 15-20 minutes until sugar layer being plain, coating the coating layer with the color required; putting the prepared color paste into the syrup for uniform mixing and then pouring the mixture into the pot; stirring the mixture uniformly for several times, 15-20 each time.

Embodiment 13 Levoisovalerylspiramycin I Syrup (Calculated in 1000 Bags)

| Formula: Levoisovalerylspiramycin I raw powder | 125 g |
|---|---|
| Citric acid (0.5%) | 1.5 g |
| Cane sugar | Total weight—other adjuvants |
| Total weight | about 50 g |
| Pigment (curcumin) | about 0.1 g |

Preparation process: crushing levoisovalerylspiramycin I raw powder, citric acid and cane sugar into granules respectively with high-speed pneumatic cracker, with 85% granules via 300-mesh sieve and 15% granules vial 80-mesh sieve, and then weighing the fine powder crushed according to the formula and fully mixing for 1-1.5 hours, measuring the content and calculating the filling amount (500 mg per bag theoretically), then filling the mixture into the bagger, filling the aluminized paper, and dispensing the mixture according to the operation requirements of dispenser, with filling difference within ±5%, and examining for qualification after filling, and finally packing.

Embodiment 14 Levoisovalerylspiramycin I Enteric-Coated Tablets (Calculated in 1000 Tablets)

Formula: refer to Embodiment 10.

Preparation process: preparing the tablet cores according to Embodiment 5; putting the conforming tablet cores into the pot for coating sugar, using 60-70% syrup and talcum powder for coating three layers as based coating layer, and then coating the isolation layer, adding 10% zein alcohol solution, drying for 10-15 minutes with rollover method, and then dropping diethyl ortho-phthalate, acetone, cellulose acetate-phthalate and alcohol solution, i.e. the intestinal solution into the pot, and drying for 2-3 times with rollover method; carrying out sugar coating according to Embodiment 13 after conforming qualification in examination.

Embodiment 15 Levoisovalerylspiramycin I Gastric-Coated Tablets (Calculated in 1000 Tablets)

Formula: refer to Embodiment 10.

Preparation process: preparing the tablet cores according to Embodiment 11; putting the conforming tablet cores into a high-efficiency coating machine, and then making the qualified coating powder (including fat soluble and water soluble) into coating solution according to the requirements, and putting the coating solution into the colloid mill for crushing, and filtering for use. Pre-heating the high-efficiency coating pot filled with tablet cores, with rotation speed within 5-10 rpm and temperature at 45~60□, spraying the coating solution into the pot with aerosol sprayer (>300 meshes), and then drying for 25-35 minutes, carrying repeatedly out the process for 8-12 times, until the coating is uniform; and finally packing after drying and conforming via inspection.

Embodiment 16 Levoisovalerylspiramycin I Granules (Calculated in 1000 Bags)

| Formula: | |
|---|---|
| Levoisovalerylspiramycin I raw powder | 125 g |
| Sugar powder | 2000 g |
| Dextrin | 900 g |
| 5% PVP-K30 | Appropriate |

Preparation process: screening the levoisovalerylspiramycin I raw powder, sugarpowder and dextrin with 120-mesh sieve, weighing levoisovalerylspiramycin I, sugar powder and dextrin according to the formula, and mixing them uniformly; making the above uniformly mixed material into soft material with 5% PVP-K30 mucilage; preparing the material into granules with oscillating granulator, drying the granules in 70□, sorting granules, and then packing them after being inspected qualified.

Embodiment 17 Preparation of Levoisovalerylspiramycin II Solution for Injection (1) uniformly mixing 100 mg isovalerylspiramycin II and adipic acid with equal mole, and dissolving into 1~5 ml distilled water to obtain light yellow and transparent solution, with a pH 4.6~5.6.

(2) adding activated carbon which is 0.1% of the solution in volume to the solution prepared in step (1), and filtering the solution;

(3) sealing, sterilizing, inspecting and packing under aseptic condition.

Embodiment 18 Preparation of Levoisovalerylspiramycin II Solution for Injection (1) uniformly mixing 100 mg isovalerylspiramycin II and citric acid with equal mole, and dissolving into 1~5 ml distilled water to obtain light yellow and transparent solution, with a pH 4.6~5.6.

(2) adding activated carbon which is 0.1% of the solution in volume to the solution prepared in step (1), and filtering the solution;

(3) sealing, sterilizing, inspecting and packing the solution under aseptic condition.

Embodiment 19 Preparation of Levoisovalerylspiramycin II Powder for Injection (1) uniformly mixing 100 mg isovalerylspiramycin II and citric acid with equal mole, and dissolving into 1~5 ml distilled water to obtain light yellow and transparent solution, with a pH 4.6~5.6.

(2) adding activated carbon which is 0.1% of the solution in volume to the solution prepared in step (1), and filtering the solution;

(3) adding 30~150 mg mannitol as lyophilization proppant; quickly freezing for 9 h under a low temperature, and drying to obtain light yellow loose lump, and then capping, inspecting and packing under aseptic condition.

Embodiment 20 Preparation of Levoisovalerylspiramycin II Tablets (Calculated in 1000 Tablets)

Formula:

| | |
|---|---|
| Levoisovalerylspiramycin II | 100 g |
| Low-substituted hydroxypropyl cellulose (5%) | 9.25 g |
| Sodium carboxymethyl starch (3%) | 5.55 g |
| Magnesium stearate (1%) | 1.85 g |
| Starch | Total weight – weight of other adjuvants |
| Total weight | 185 g |

Preparation process: weighing appropriate starch and diluting to 15% concentration, heating until paste to prepare adhesive; sieving the active ingredient carrimycin, adjuvants containing starch, low-substituted hydroxypropyl cellulose, sodium carboxymethyl starch and magnesium stearate respectively with a 100-mesh sieve, and weighing the active ingredient and adjuvants required according to the formula; fully mixing levoisovalerylspiramycin II, starch and low-substituted hydroxypropyl cellulose, using 15% starch paste to prepare soft material, making the soft material into granules with 14-mesh sieve, drying under 50-60□ until water content at 3-5%; sorting the granules with 14-mesh sieve, and adding and mixing sodium carboxymethyl starch and magnesium stearate, determining the content of granules; calculating the weight of each tablet according to the content of granules; pressing the tablets (Φ9 mm dimple punch), detecting the tablet weight difference, and then packing the qualified tablets after detection.

Embodiment 21 Preparation of Levoisovalerylspiramycin II Capsules (Calculated in 1000 Capsules)

Formula:

| | |
|---|---|
| Levoisovalerylspiramycin II raw powder | 100 g |
| Starch (for pharmaceutical purpose) | 108 g – levoisovalerylspiramycin II raw powder weight |
| Pharmaceutical No.3 capsule | 100 capsules |
| Liquid paraffin | 5 ml |

Preparation process: weighing the active ingredient levoisovalerylspiramycin II, adjuvant starch (for pharmaceutical use) respectively according to the formula and then putting them into a mixer to fully mix for 1.5-2 hours; the data of sample content detected should be basically consistent with the theoretical data (about 0.105 g for each capsule). Filling the conforming pharmaceutical No. 3 capsule and mixed material to into the filler for filling according to the operation requirements of full-automatic capsule machine; detecting the difference of the filled capsules (within ±10%, <0.3 g) and dissolution rate, putting the conforming capsules into the glazing machine and adding liquid paraffin for glazing for 15-20 minutes, and then taking out for detection of finished product packing box.

Embodiment 22 Preparation of Isovalerylspiramycin III Solution for Injection (1) uniformly mixing 100 mg isovalerylspiramycin III and maleic acid with equal mole, and dissolving into 1~5 ml distilled water to obtain light yellow and transparent solution, with a pH 4.6~5.6.

(2) adding activated carbon which is 0.1% of the solution in volume to the solution prepared in step (1), and filtering the solution;

(3) sealing, sterilizing, inspecting and packing under aseptic condition.

Embodiment 23 Preparation of Levoisovalerylspiramycin III Powder for Injection (1) uniformly mixing 100 mg isovalerylspiramycin III and maleic acid with equal mole, and dissolving into 1~5 ml distilled water to obtain light yellow and transparent solution, with a pH 4.6~5.6.

(2) adding activated carbon which is 0.1% of the solution in volume to the solution prepared in step (1), and filtering the solution;

(3) add 30~150 mg mannitol as lyophilization proppant; quickly freezing for 9 h under a low temperature, and drying to obtain light yellow loose lump, then capping, inspecting and packing under aseptic condition.

Embodiment 24 Levoisovalerylspiramycin III Capsules (Calculated in 1000 Capsules)

Formula:

| | |
|---|---|
| Levoisovalerylspiramycin III raw powder | 100 g |
| Starch (for pharmaceutical use) | 108 g – levoisovalerylspiramycin III raw powder weight |
| Pharmaceutical No.3 capsule | 100 capsules |
| Liquid paraffin | 5 ml |

Preparation process: weighing the active ingredient levoisovalerylspiramycin III, adjuvant starch (for pharmaceutical use) respectively according to the formula, and then putting them into a mixer for fully mixing for 1.5-2 hours; the data of sample content detected should be basically consistent with the theoretical data (about 0.105 g for each capsule). Filling the conforming pharmaceutical No. 3 capsule and mixed material into the filler for filling according to the operation requirements of full-automatic capsule machine; detecting the difference of the filled capsules (within ±10%, <0.3 g) and dissolution rate, putting the conforming capsules into the glazing machine and adding liquid paraffin for glazing for 15-20 minutes, and then taking out for detection of finished product packing box.

Embodiment 25 Levoisovalerylspiramycin III Syrup (Calculated in 1000 Bags)

Formula:

| Levoisovalerylspiramycin I raw powder | 125 g |
|---|---|
| Citric acid (0.5%) | 1.5 g |
| Cane sugar | Total weight – other raw and adjuvant materials |
| Total weight | 50 g |
| Pigment (curcumin) | about 0.1 g |

Preparation process: crushing levoisovalerylspiramycin III raw powder, citric acid and cane sugar into granules respectively with high-speed pneumatic cracker, with 85% granules via 300-mesh sieve and 15% granules via 180-mesh sieve, and then weighing the fine crushed powder according to the formula and fully mixing for 1-1.5 hours, measuring the content and calculating the filling amount (500 mg per bag theoretically), then filling the mixture into the bagger, and filling the aluminized paper, and dispensing the mixture according to the operation requirements of dispenser, with filling difference within ±5%, examining for qualification after filling, and finally packing.

Embodiment 26 Levoisovalerylspiramycin III Granules (Calculated in 1000 Bags)

Formula:

| Levoisovalerylspiramycin III raw powder | 125 g |
|---|---|
| Sugar powder | 2000 g |
| Dextrin | 900 g |
| 5% PVP-K30 | Appropriate |

Preparation process: screening levoisovalerylspiramycin III raw powder, sugar powder and dextrin with 120-mesh sieve, weighing levoisovalerylspiramycin III, sugar powder and dextrin according to the formula and mixing them uniformly; making the above uniformly mixed material into soft material with 5% PVP-K30 mucilage; preparing the material into granules with oscillating granulator, drying the granules in 70□, sorting granules, and then packing them after being inspected qualified.

Embodiment 27

Further make the white solid powder levoisovalerylspiramycin I in Embodiment 1 into crystal. Preparation method of crystalline compound of levoisovalerylspiramycin I:

1. first dissolving solid levoisovalerylspiramycin I obtained in Embodiment 1 in a mixed solvent of ethyl acetate, absolute ethyl alcohol and anhydrous acetone, with volume proportion of 1:10:1;

2. then adding pure water and stirring the mixture simultaneously, and the volume of added pure water is 2.5 times of total volume of ethyl acetate, absolute ethyl alcohol and anhydrous acetone; the adding velocity of water is 4 ml/min; and the stirring rate of adding pure water is 30 r/min;

3. cooling to 5□ with speed of 1□/h after adding pure water, continuing stirring when cooling, to obtain crystalline compound of levoisovalerylspiramycin I.

Figure 5:
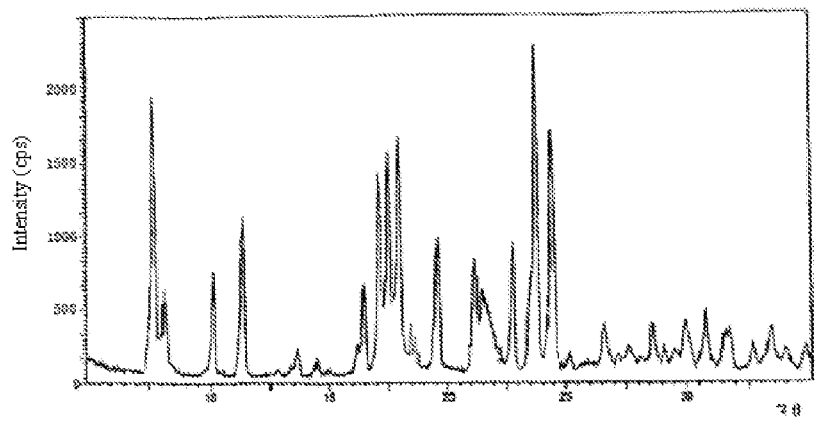
FIG. 5 shows the X-ray powder diffraction diagram of levoisovalerylspiramycin I of the present invention.

The X-ray powder diffraction of crystalline compound of levoisovalerylspiramycin I measured by Cu-Ka ray has characteristic peaks at 2θ being 7.6°, 8.0°, 10.0°, 11.4°, 16.4°, 17.0°, 17.5°, 17.9°, 19.5°, 22.7°, 23.7° and 24.4°, and the diffraction spectrum of X-ray is as shown in FIG. 5.

Embodiment 28

Further make the white solid powder levoisovalerylspiramycin I in Embodiment 1 into crystal.

Preparation method of crystalline compound of levoisovalerylspiramycin I:

1. first dissolving solid levoisovalerylspiramycin I in a mixed solvent of ethyl acetate, absolute ethyl alcohol and anhydrous acetone, with volume proportion of 1:10:1;

2. then adding pure water and stirring the mixture simultaneously, and the volume of added pure water is 9 times of total volume of ethyl acetate, absolute ethyl alcohol and anhydrous acetone; the adding velocity of water is 10 ml/min; and the stirring rate of adding pure water is 60 r/min;

3. cooling to 15□ with speed of 3 □/h after adding pure water, continuing stirring with rate of 10 r/min when cooling, to obtain crystalline compound of levoisovalerylspiramycin I.

The X-ray powder diffraction of crystalline compound of levoisovalerylspiramycin I measured by Cu-Ka ray is similar to FIG. 5.

Embodiment 29 Preparation Method of Solution for Injection of the Crystalline Compound of Levoisovalerylspiramycin I Make crystalline compound of levoisovalerylspiramycin I in Embodiment 27 into solution for injection, with preparation method ditto.

Embodiment 30 Preparation Method of Powder for Injection of the Crystalline Compound of Levoisovalerylspiramycin I Make crystalline compound of levoisovalerylspiramycin I in Embodiment 28 into powder for injection, with preparation method ditto.

Embodiment 31 Preparation Method of Tablets of the Crystalline Compound Levoisovalerylspiramycin I Make crystalline compound of levoisovalerylspiramycin I in Embodiment 27 into tablets, with preparation method ditto.

Embodiment 32

Further make the white solid powder levoisovalerylspiramycin II in Embodiment 1 into crystal.

Preparation Method of Crystalline Compound of Levoisovalerylspiramycin II:

1. first dissolving solid levoisovalerylspiramycin II in Embodiment 1 in a mixed solvent of absolute methanol, absolute ethyl alcohol and anhydrous acetone, with volume proportion of 1:10:1;

2. then adding pure water and stirring the mixture simultaneously, and the volume of added pure water is 2.5 times of total volume of absolute methanol, absolute ethyl alcohol and anhydrous acetone; the adding velocity of water is 4 ml/min; and the stirring rate of adding pure water is 30 r/min;

3. cooling to 5□ with speed of 1 □/h after adding pure water, continuing stirring with rate of 10 r/min when cooling, to obtain crystalline compound of levoisovalerylspiramycin II.

Figure 6:
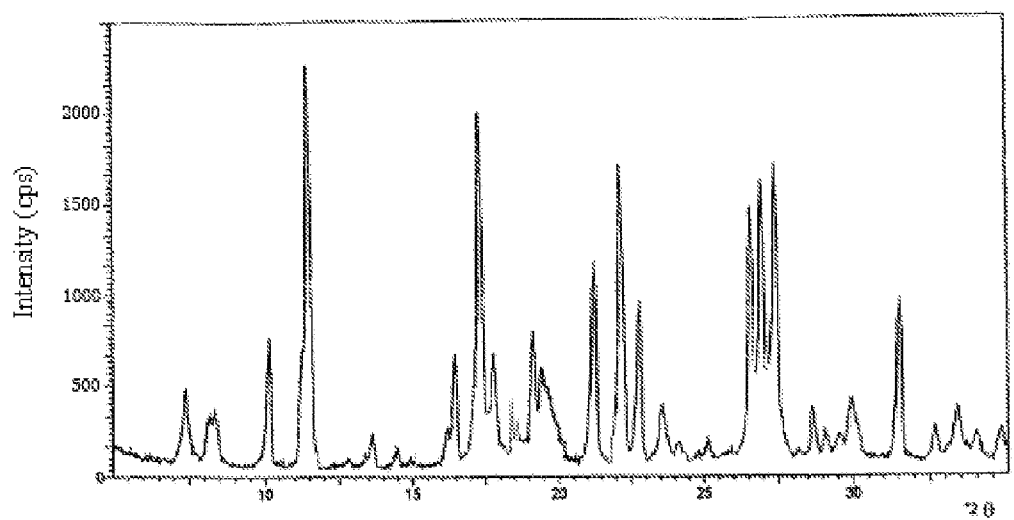
FIG. 6 shows the X-ray powder diffraction diagram of levoisovalerylspiramycin II of the present invention.

The X-ray powder diffraction of crystalline compound levoisovalerylspiramycin II measured by Cu-Ka ray has characteristic peaks when 2θ being 10.0°, 11.6°, 16.4°, 17.3°, 19.1°, 21.2°, 22.1°, 22.7°, 26.4°, 26.9°, 27.5° and 31.5°, and the diffraction spectrum of X-ray is as shown in FIG. 6.

Embodiment 33

Further make the white solid powder levoisovalerylspiramycin II in Embodiment 1 into crystal.

Preparation Method of Crystalline Compound of Levoisovalerylspiramycin II:

1. first dissolving solid levoisovalerylspiramycin II in Embodiment 1 in a mixed solvent of absolute methanol, absolute ethyl alcohol and anhydrous acetone, with volume proportion of 1:10:0.8;

2. then adding pure water and stirring the mixture simultaneously, and the volume of added pure water is 9 times of total volume of absolute methanol, absolute ethyl alcohol and anhydrous acetone; the adding velocity of water is 10 ml/min; and the stirring rate of pure water added is 60 r/min;

3. cooling to 15□ with speed of 3 □/h after adding pure water, continuing stirring with rate of 10 r/min when cooling, to obtain crystalline compound of levoisovalerylspiramycin II.

The X-ray powder diffraction of crystalline compound of levoisovalerylspiramycin II measured by Cu-Ka ray is similar to FIG. 6.

Embodiment 34

Further make the white solid powder levoisovalerylspiramycin II in Embodiment 2 into crystal.

Preparation Method of Crystalline Compound of Levoisovalerylspiramycin II:

1. first dissolving solid levoisovalerylspiramycin II in a mixed solvent of absolute methanol, absolute ethyl alcohol and anhydrous acetone, with volume proportion of 1:5:1;

2. then adding pure water and stirring the mixture simultaneously, and the volume of added pure water is 7.5 times of total volume of absolute methanol, absolute ethyl alcohol and anhydrous acetone; the adding velocity of water is 6 ml/min; and the stirring rate of adding pure water is 40 r/min;

3. cooling to 10□ with speed of 2 □/h after adding pure water, continuing stirring with rate of 15 r/min when cooling, to obtain crystalline compound of levoisovalerylspiramycin II.

The X-ray powder diffraction of crystalline compound of levoisovalerylspiramycin II measured by Cu-Ka ray is similar to FIG. 6.

Embodiment 35

Further make the white solid powder levoisovalerylspiramycin II in Embodiment 3 into crystal.

Preparation Method of Crystalline Compound of Levoisovalerylspiramycin II:

1. first dissolving solid levoisovalerylspiramycin II in a mixed solvent of absolute methanol, absolute ethyl alcohol and anhydrous acetone, with volume proportion of 1:3:1;

2. then adding pure water and stirring the mixture simultaneously, and the volume of added pure water is 7.5 times of total volume of absolute methanol, absolute ethyl alcohol and anhydrous acetone; the adding velocity of water is 8 ml/min; and the stirring rate of adding pure water is 45 r/min;

3. cooling to 12□ with speed of 2.5 □/h after adding pure water, continuing stirring with rate of 20 r/min when cooling, to obtain crystalline compound of levoisovalerylspiramycin II.

The X-ray powder diffraction of crystalline compound of levoisovalerylspiramycin II measured by Cu-Ka ray is similar to FIG. 6.

Embodiment 36

Further make the white solid powder levoisovalerylspiramycin II in Embodiment 3 into crystal.

Preparation Method of Crystalline Compound of Levoisovalerylspiramycin II:

1. first dissolving solid levoisovalerylspiramycin II in a mixed solvent of absolute methanol, absolute ethyl alcohol and anhydrous acetone, with volume proportion of 1:6:0.8;

2. then adding pure water and stirring the mixture simultaneously, and the volume of added pure water is 5 times of total volume of absolute methanol, absolute ethyl alcohol and anhydrous acetone; the adding velocity of water is 7 ml/min; and the stirring rate of adding pure water is 60 r/min;

3. cooling to 12□ with speed of 1.2 □/h after adding pure water, continuing stirring with rate of 15 r/min when cooling, to obtain crystalline compound of levoisovalerylspiramycin The X-ray powder diffraction of crystalline compound of levoisovalerylspiramycin II measured by Cu-Ka ray is similar to FIG. 5.

Embodiment 37 Preparation Method of Solution for Injection of the Crystalline Compound of Levoisovalerylspiramycin II Make crystalline compound of levoisovalerylspiramycin II in Embodiment 34 into solution for injection, with preparation method ditto.

Embodiment 38 Preparation Method of Solution for Injection of the Crystalline Compound of Levoisovalerylspiramycin II Make crystalline compound of levoisovalerylspiramycin II in Embodiment 33 into solution for injection, with preparation method ditto.

Embodiment 39 Preparation Method of Powder for Injection of the Crystalline Compound of Levoisovalerylspiramycin II Make crystalline compound of levoisovalerylspiramycin II in Embodiment 36 into powder for injection, with preparation method ditto.

Embodiment 40 Preparation Method of Powder for Injection of the Crystalline Compound of Levoisovalerylspiramycin II Make crystalline compound of levoisovalerylspiramycin II in Embodiment 35 into powder for injection, with preparation method ditto.

Embodiment 41 Preparation Method of Tablets of the Crystalline Compound of Levoisovalerylspiramycin II Make crystalline compound of levoisovalerylspiramycin II in Embodiment 36 into tablets, with preparation method ditto.

Embodiment 42 Preparation Method of Capsules of the Crystalline Compound of Levoisovalerylspiramycin II Make crystalline compound of levoisovalerylspiramycin II in Embodiment 32 into capsules, with preparation method ditto.

Embodiment 43 Preparation Method of Granules of the Crystalline Compound of Levoisovalerylspiramycin II Make crystalline compound of levoisovalerylspiramycin II in Embodiment 33 into granules, with preparation method ditto.

Embodiment 44

Further make the white solid powder levoisovalerylspiramycin III in Embodiment 1 into crystal.

Preparation Method of Crystalline Compound of Levoisovalerylspiramycin III:

1. first dissolving solid levoisovalerylspiramycin III in Embodiment 1 in a mixed solvent of absolute methanol, absolute ethyl alcohol and anhydrous acetone, with volume proportion of 1:10:1;

2. then adding pure water and stirring the mixture simultaneously, and the volume of added pure water is 2.5 times of total volume of absolute methanol, absolute ethyl alcohol and anhydrous acetone; the velocity of water adding is 4 ml/min; and the stirring rate of adding pure water is 30 r/min;

3. cooling to 5□ with speed of 1 □/h after adding pure water, continuing stirring with rate of 10 r/min when cooling, to obtain crystalline compound of levoisovalerylspiramycin III.

Figure 7:
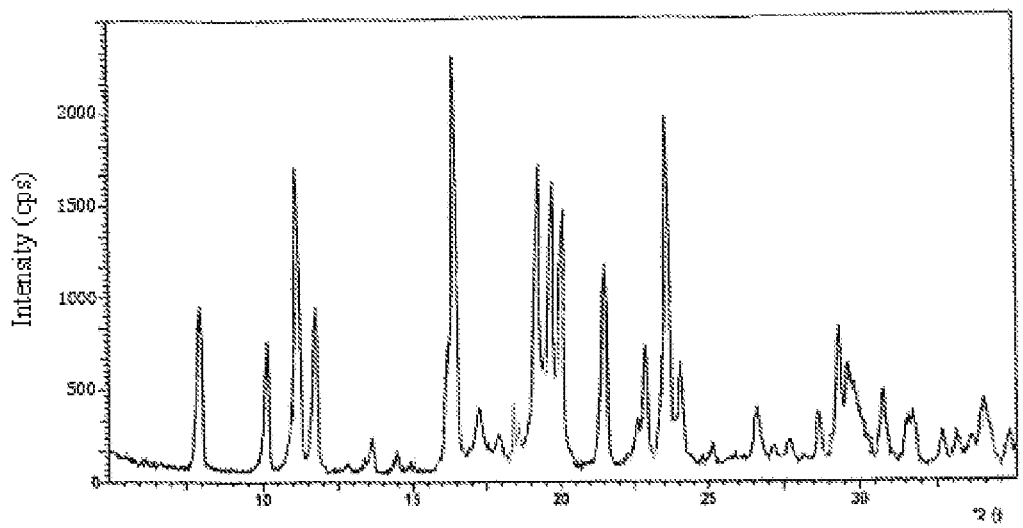
FIG. 7 shows the X-ray powder diffraction diagram of levoisovalerylspiramycin III of the present invention.

The X-ray powder diffraction of crystalline compound of levoisovalerylspiramycin III measured by Cu-Ka ray has characteristic peaks at 2θ being 8.0°, 10.0°, 11.2°, 11.7°, 16.4°, 19.1°, 19.6°, 20.0°, 21.4°, 22.9°, 23.6° and 29.4°, and the diffraction spectrum of X-ray is as shown in FIG. 7.

Embodiment 45

Further make the white solid powder levoisovalerylspiramycin III in Embodiment 2 into crystal.

Preparation Method of Crystalline Compound of Levoisovalerylspiramycin III:

1. first dissolving solid levoisovalerylspiramycin III in a mixed solvent of absolute methanol, absolute ethyl alcohol and anhydrous acetone, with volume proportion of 1:10:1;

2. then adding pure water and stirring the mixture simultaneously, and the volume of added pure water is 9 times of total volume of absolute methanol, absolute ethyl alcohol and anhydrous acetone; the adding velocity of water is 10 ml/min; and the stirring rate of adding pure water is 60 r/min;

3. cooling to 15□ with speed of 3 □/h after adding pure water, continuing stirring with rate of 10 r/min when cooling, to obtain crystalline compound of levoisovalerylspiramycin III.

The X-ray powder diffraction of crystalline compound of levoisovalerylspiramycin III measured by Cu-Ka ray is similar to FIG. 7.

Embodiment 46

Further make the white solid powder levoisovalerylspiramycin III in Embodiment 2 into crystal.

Preparation Method of Crystalline Compound of Levoisovalerylspiramycin III:

1. first dissolving solid levoisovalerylspiramycin III in a mixed solvent of absolute methanol, absolute ethyl alcohol and anhydrous acetone, with volume proportion of 1:5:0.8;

2. then adding pure water and stirring the mixture simultaneously, and the volume of added pure water is 7.5 times of total volume of absolute methanol, absolute ethyl alcohol and anhydrous acetone; the adding velocity of water is 6 ml/min; and the stirring rate of adding pure water is 40 r/min;

3. cooling to 10□ with speed of 2 □/h after adding pure water, continuing stirring with rate of 15 r/min when cooling, to obtain crystalline compound of levoisovalerylspiramycin III.

The X-ray powder diffraction of crystalline compound of levoisovalerylspiramycin III measured by Cu-Ka ray is similar to FIG. 7.

Embodiment 47

Further make the levoisovalerylspiramycin III white solid powder prepared in Embodiment 3 into crystal.

Preparation Method of Crystalline Compound of Levoisovalerylspiramycin III:

1. first dissolving solid levoisovalerylspiramycin III in a mixed solvent of absolute methanol, absolute ethyl alcohol and anhydrous acetone, with volume proportion of 1:2:1;

2. then adding pure water and stirring the mixture simultaneously, and the volume of added pure water is 7.5 times of total volume of absolute methanol, absolute ethyl alcohol and anhydrous acetone; the adding velocity of water is 8 ml/min; and the stirring rate of adding pure water is 45 r/min;

3. cooling to 12□ with speed of 2.5 □/h after adding pure water, continuing stirring with rate of 20 r/min when cooling, to obtain crystalline compound of levoisovalerylspiramycin III.

The X-ray powder diffraction of crystalline compound of levoisovalerylspiramycin III measured by Cu-Ka ray is similar to FIG. 7.

Embodiment 48 Preparation Method of Solution for Injection of the Crystalline Compound of Levoisovalerylspiramycin III Make crystalline compound of levoisovalerylspiramycin III in Embodiment 44 into solution for injection, with preparation method ditto.

Embodiment 49 Preparation Method of Powder for Injection of the Crystalline Compound of Levoisovalerylspiramycin III Make crystalline compound of levoisovalerylspiramycin III in Embodiment 45 into powder for injection, with preparation method ditto.

Embodiment 50 Preparation Method of Tablets of the Crystalline Compound of Levoisovalerylspiramycin III Make crystalline compound of levoisovalerylspiramycin III in Embodiment 46 into tablets, with preparation method ditto.

Embodiment 51 Preparation Method of Capsules of the Crystalline Compound of Levoisovalerylspiramycin III Make crystalline compound of levoisovalerylspiramycin III in Embodiment 47 into capsules, with preparation method ditto.

Test 1 Acute Toxicity Test of Levoisovalerylspiramycin I, II and III

1. Test Method:

Both mice and rats take drugs orally (levoisovalerylspiramycin I, II and III prepared in Embodiment 1)

After observing the mice and rats for two days before test, and those without abnormal conditions is carried out test. Don't give anything to eat to mice and rats overnight before test. According to prediction result, respectively feed 4000 mg/kg experimental drugs to mice and rats via intragastric administration, without any death. In this test, feed drugs to mice and rats respectively as per 4000 mg/kg, wherein, mice follow 100 mg/ml, with intragastric administration capacity of 0.6-0.8 ml per one, while rats 173 mg/ml, with intragastric administration capacity of 0.8~1.0 ml/50 g. Observe those taking drugs for one week for toxic reaction and death.

II. See Table 1 and 2 for Test Results

TABLE 1

Acute toxicity of experimental drugs on mice via oral administration ($LD_{50}$)

| Experimental drug | Dosage (mg/kg) | Quantity | mortality | Mortality rate (%) | $LD_{50}$ (mg/kg) |
| --- | --- | --- | --- | --- | --- |
| Levoisovalerylspiramycin I | 4000 | 20 | 7 | 35 | >4000 |
| Levoisovalerylspiramycin II | 4000 | 20 | 7 | 35 | >4000 |
| Levoisovalerylspiramycin III | 4000 | 20 | 7 | 35 | >4000 |

TABLE 2

Acute toxicity of experimental drugs on rats via oral administration ($LD_{50}$)

| Experimental drug | Dosage (mg/kg) | Quantity | mortality | Mortality rate (%) | LD50 (mg/kg) |
| --- | --- | --- | --- | --- | --- |
| Levoisovalerylspiramycin I | 4500 | 20 | 3 | 15 | >4500 |

TABLE 2-continued

Acute toxicity of experimental drugs on rats via oral administration (LD$_{50}$)

| Experimental drug | Dosage (mg/kg) | Quantity | mortality | Mortality rate (%) | LD50 (mg/kg) |
|---|---|---|---|---|---|
| Levoisovaleryl-spiramycin II | 4500 | 20 | 3 | 15 | >4500 |
| Levoisovaleryl-spiramycin III | 4500 | 20 | 3 | 15 | >4500 |

The same test also has been carried out for levoisovalerylspiramycin I, II and III or levoisovalerylspiramycin I, II, III preparations prepared in other embodiments of this invention, and the results obtained are similar.

Test Example 2: In Vivo Effect of Levoisovalerylspiramycin I and its Crystal

Test method: preparation of infection bacterial liquid: taking out the test bacterial liquid which is kept in a refrigerator at −80☐ to room temperature for about 1 h, then inoculating *streptococcus pneumonia*, pyogenic *streptococcus* and *enterococcus* absorbing 0.1 ml bacterial liquid respectively to 2 ml MH broth (add 10% inactivated horse serum), and inoculating 0.1 ml bacterial liquid of *staphylococcus aureus* to 2 ml MH broth according to the same method above; putting it in an incubator at 37☐ to be cultivated for 18 h, to obtain original bacterial liquid; diluting the original bacterial liquid with 5% gastric mucin to make animals infected with 100% lethal bacteria, to obtain infection bacterial liquid.

The clinical route of administration of carrimycin is proposed to be oral administration, thus intragastric administration is adopted in carrimychin test. Levoisovalerylspiramycin I (obtained in Embodiment 1) and of crystalline compound of levoisovalerylspiramycin I (prepared in Embodiment 27) are fed to animals via intramuscular injection.

After fed a 0.5 ml lethal dose to mice via intraperitoneal injection; they develop symptoms of significantly reduced activities, repose and fur loosening etc. After the mice are infected, respectively feed each mouse 0.2 ml via intragastric administration at 0.5 to 6 h, and they have no adverse reaction. Observe the number of deaths in 7 days, and calculate the 50% effective dose (ED$_{50}$) of each drug for the infected mouse and compare the protective effect of drugs by Bliss program.

Result of In Vivo Test:

TABLE 3

Comparison of curative effects of 5 antibiotics on mouse with abdominal infection of 6 strains of *streptococci*

| Test organism | Challenging dose (CFU/0.5 ml/rat) | Drug | MIC (μg/ml) | ED$_{50}$ (mg/kg) |
|---|---|---|---|---|
| *streptococcus pneumoniae*3 | 6.4 × 10$^4$ | isovalerylspiramycin I | 0.12 | 9.73 |
| | | crystal of isovalerylspiramycin I | 0.12 | 8.39 |
| | | carrimychin | 0.12 | 10.41 |
| | | azithromycin | 0.12 | 18.29 |
| | | acetyl spiramycin | 0.5 | 66.96 |
| | | erythrocin | 1 | 85.08 |
| *streptococcus pneumoniae*18 | 9.6 × 10$^4$ | isovalerylspiramycin I | 0.03 | 9.51 |
| | | crystal of isovalerylspiramycin I | 0.03 | 8.65 |
| | | carrimychin | 0.03 | 10.06 |
| | | azithromycin | 0.06 | 14.87 |
| | | acetyl spiramycin | 0.06 | 37.93 |
| | | erythrocin | 0.06 | 57.08 |
| *streptococcus pneumoniae*57 | 8.8 × 10$^4$ | isovalerylspiramycin I | 0.06 | 13.86 |
| | | crystal of isovalerylspiramycin I | 0.06 | 12.82 |
| | | carrimychin | 0.12 | 16.02 |
| | | azithromycin | 0.12 | 19.02 |
| | | acetyl spiramycin | 1 | 398.01 |
| | | erythrocin | 0.25 | 102.33 |
| pyogenic *streptococcus* 772 | 6.9 × 10$^3$ | isovalerylspiramycin I | 0.06 | 26.15 |
| | | crystal of isovalerylspiramycin I | 0.06 | 23.37 |
| | | carrimychin | 0.12 | 26.30 |
| | | azithromycin | 0.25 | 46.89 |
| | | acetyl spiramycin | 0.25 | 98.11 |
| | | erythrocin | 0.5 | 101.33 |
| pyogenic *streptococcus* 102 | 7.8 × 10$^4$ | isovalerylspiramycin I | 0.12 | 66.40 |
| | | crystal of isovalerylspiramycin I | 0.12 | 60.99 |
| | | carrimychin | 0.25 | 87.84 |
| | | azithromycin | 0.5 | 159.06 |
| | | acetyl spiramycin | 0.5 | 227.07 |
| | | erythrocin | 0.5 | 361.01 |
| pyogenic *streptococcus* 119 | 4.9 × 10$^4$ | isovalerylspiramycin I | 0.12 | 57.25 |
| | | crystal of isovalerylspiramycin I | 0.12 | 54.58 |
| | | carrimychin | 0.25 | 68.48 |
| | | azithromycin | 0.25 | 68.48 |
| | | acetyl spiramycin | 0.5 | 117.53 |
| | | erythrocin | 0.5 | 233.72 |

TABLE 4

Comparison of curative effects of 5 antibiotics on mouse with abdominal infection of *enterococcus* and *staphylococcus aureus*

| Test organism | Challenging dose (CFU/0.5 ml/rat) | Drug | MIC (μg/ml) | $ED_{50}$ (mg/kg) |
|---|---|---|---|---|
| *enterococcus*32 | $5.4 \times 10^4$ | isovalerylspiramycin I | 0.5 | 77.55 |
| | | crystal of isovalerylspiramycin I | 0.5 | 62.11 |
| | | carrimychin | 0.5 | 89.29 |
| | | azithromycin | 1 | 146.51 |
| | | acetyl spiramycin | 1 | 130.34 |
| | | erythrocin | 2 | 175.23 |
| *staphylococcus aureus*16 | $5.2 \times 10^3$ | isovalerylspiramycin I | 0.5 | 23.54 |
| | | crystal of isovalerylspiramycin I | 0.5 | 21.33 |
| | | carrimychin | 0.5 | 31.98 |
| | | azithromycin | 0.5 | 31.98 |
| | | acetyl spiramycin | 1 | 43.58 |
| | | erythrocin | 1 | 82.36 |
| *staphylococcus aureus*76 | $5.8 \times 10^4$ | isovalerylspiramycin I | 0.5 | 24.40 |
| | | crystal of isovalerylspiramycin I | 0.5 | 22.26 |
| | | carrimychin | 0.5 | 31.50 |
| | | azithromycin | 1 | 58.79 |
| | | acetyl spiramycin | 1 | 66.63 |
| | | erythrocin | 1 | 64.17 |
| *staphylococcus aureus*12 | $4.8 \times 10^4$ | isovalerylspiramycin I | 1 | 110.24 |
| | | crystal of isovalerylspiramycin I | 1 | 107.46 |
| | | carrimychin | 2 | 120.35 |
| | | azithromycin | 2 | 120.35 |
| | | acetyl spiramycin | 2048 | >500 |
| | | erythrocin | 256 | 266.11 |
| *staphylococcus aureus*21 | $4.2 \times 10^4$ | isovalerylspiramycin I | 0.5 | 42.67 |
| | | crystal of isovalerylspiramycin I | 0.5 | 38.00 |
| | | carrimychin | 1 | 59.30 |
| | | azithromycin | 4 | 142.99 |
| | | acetyl spiramycin | 2048 | >500 |
| | | erythrocin | 4 | 213.67 |

Results of In Vivo Test:

Refer to Table 3 and Table 4 for the curative effect of isovalerylspiramycin I on mouse infected with 12 strains of bacteria, which shows a good protective effect; and the crystalline compound of isovalerylspiramycin I shows a better protective effect on mouse infected with 12 strains of bacteria.

Same test is conducted for levoisovalerylspiramycin I and crystal of levoisovalerylspiramycin I prepared in other embodiments of the present invention or preparations containing levoisovalerylspiramycin I or its crystal, the results are similar.

Test Example 3: In Vivo Effect of Levoisovalerylspiramycin II and its Crystalline Compound Adopt the levoisovalerylspiramycin II prepared in Embodiment 1 and crystalline compound of levoisovalerylspiramycin II prepared in Embodiment 36, and the test method is same as that in test example 2.

Refer to Table 5 and Table 6 for the Results of In Vivo Test:

TABLE 5

Comparison of curative effects of 5 antibiotics on mouse with abdominal infection of 6 strains of *streptococci*

| Test organism | Challenging dose (CFU/0.5 ml/rat) | Drug | MIC (μg/ml) | $ED_{50}$ (mg/kg) |
|---|---|---|---|---|
| *streptococcus pneumoniae*3 | $6.4 \times 10^4$ | isovalerylspiramycin II | 0.12 | 8.99 |
| | | crystal of isovalerylspiramycin II | 0.12 | 7.69 |
| | | carrimychin | 0.12 | 10.41 |
| | | azithromycin | 0.12 | 18.29 |
| | | acetyl spiramycin | 0.5 | 66.96 |
| | | erythrocin | 1 | 85.08 |
| *streptococcus pneumoniae*18 | $9.6 \times 10^4$ | isovalerylspiramycin II | 0.03 | 8.98 |
| | | crystal of isovalerylspiramycin II | 0.03 | 8.09 |
| | | carrimychin | 0.03 | 10.06 |
| | | azithromycin | 0.06 | 14.87 |
| | | acetyl spiramycin | 0.06 | 37.93 |
| | | erythrocin | 0.06 | 57.08 |
| *streptococcus pneumoniae*57 | $8.8 \times 10^4$ | isovalerylspiramycin II | 0.06 | 13.10 |
| | | crystal of isovalerylspiramycin II | 0.06 | 12.04 |
| | | carrimychin | 0.12 | 16.02 |
| | | azithromycin | 0.12 | 19.02 |
| | | acetyl spiramycin | 1 | 398.01 |
| | | erythrocin | 0.25 | 102.33 |
| *pyogenic* | $6.9 \times 10^3$ | isovalerylspiramycin II | 0.06 | 24.61 |

TABLE 5-continued

Comparison of curative effects of 5 antibiotics on mouse with abdominal infection of 6 strains of *streptococci*

| Test organism | Challenging dose (CFU/0.5 ml/rat) | Drug | MIC (µg/ml) | $ED_{50}$ (mg/kg) |
|---|---|---|---|---|
| *streptococcus*$_{772}$ | | crystal of isovalerylspiramycin II | 0.06 | 21.90 |
| | | carrimychin | 0.12 | 26.30 |
| | | azithromycin | 0.25 | 46.89 |
| | | acetyl spiramycin | 0.25 | 98.11 |
| | | erythrocin | 0.5 | 101.33 |
| *pyogenic streptococcus*$_{102}$ | $7.8 \times 10^4$ | isovalerylspiramycin II | 0.12 | 63.21 |
| | | crystal of isovalerylspiramycin II | 0.12 | 58.00 |
| | | carrimychin | 0.25 | 87.84 |
| | | azithromycin | 0.5 | 159.06 |
| | | acetyl spiramycin | 0.5 | 227.07 |
| | | erythrocin | 0.5 | 361.01 |
| *pyogenic streptococcus*$_{119}$ | $4.9 \times 10^4$ | isovalerylspiramycin II | 0.12 | 52.77 |
| | | crystal of isovalerylspiramycin II | 0.12 | 49.94 |
| | | carrimychin | 0.25 | 68.48 |
| | | azithromycin | 0.25 | 68.48 |
| | | acetyl spiramycin | 0.5 | 117.53 |
| | | erythrocin | 0.5 | 233.72 |

TABLE 6

Comparison of curative effects of 5 antibiotics on mouse with abdominal infection of *enterococcus* and *staphylococcus aureus*

| Test organism | Challenging dose (CFU/0.5 ml/rat) | Drug | MIC (µg/ml) | $ED_{50}$ (mg/kg) |
|---|---|---|---|---|
| *enterococcus*$_{32}$ | $5.4 \times 10^4$ | isovalerylspiramycin II | 0.25 | 70.16 |
| | | crystal of isovalerylspiramycin II | 0.25 | 56.16 |
| | | carrimychin | 0.5 | 89.29 |
| | | azithromycin | 1 | 146.51 |
| | | acetyl spiramycin | 1 | 130.34 |
| | | erythrocin | 2 | 175.23 |
| *staphylococcus aureus*$_{16}$ | $5.2 \times 10^3$ | isovalerylspiramycin II | 0.25 | 20.87 |
| | | crystal of isovalerylspiramycin II | 0.25 | 16.18 |
| | | carrimychin | 0.5 | 31.98 |
| | | azithromycin | 0.5 | 31.98 |
| | | acetyl spiramycin | 1 | 43.58 |
| | | erythrocin | 1 | 82.36 |
| *staphylococcus aureus*$_{76}$ | $5.8 \times 10^4$ | isovalerylspiramycin II | 0.25 | 22.26 |
| | | crystal of isovalerylspiramycin II | 0.25 | 18.71 |
| | | carrimychin | 0.5 | 31.50 |
| | | azithromycin | 1 | 58.79 |
| | | acetyl spiramycin | 1 | 66.63 |
| | | erythrocin | 1 | 64.17 |
| *staphylococcus aureus*$_{12}$ | $4.8 \times 10^4$ | isovalerylspiramycin II | 1 | 108.04 |
| | | crystal of isovalerylspiramycin II | 1 | 104.67 |
| | | carrimychin | 2 | 120.35 |
| | | azithromycin | 2 | 120.35 |
| | | acetyl spiramycin | 2048 | >500 |
| | | erythrocin | 256 | 266.11 |
| *staphylococcus aureus*$_{21}$ | $4.2 \times 10^4$ | isovalerylspiramycin II | 0.5 | 38.90 |
| | | crystal of isovalcrylspiramycin II | 0.5 | 36.09 |
| | | carrimychin | 1 | 59.30 |
| | | azithromycin | 4 | 142.99 |
| | | acetyl spiramycin | 2048 | >500 |
| | | erythrocin | 4 | 213.67 |

Results of In Vivo Test:

Refer to Table 13 and Table 14 for the curative effect of crystalline compound of isovalerylspiramycin II on mouse infected with 12 strains of bacteria, which shows a good protective effect, an effect better than the compound of isovalerylspiramycin II.

Same test is conducted for crystalline compound of levoisovalerylspiramycin II and preparation thereof prepared in other embodiments of the present invention, the results are similar.

Test Example 4: In Vivo Effect of Levoisovalerylspiramycin III and its Crystalline Compound Adopt the levoisovalerylspiramycin III in Embodiment 1 and crystalline compound of levoisovalerylspiramycin III in Embodiment 45, and the test method is same as that in test example 2.

Refer to Table 7 and Table 8 for the Results of In Vivo Test:

TABLE 7

Comparison of curative effects of 5 antibiotics on mouse with abdominal infection of 6 strains of *streptococci*

| Test organism | Challenging dose (CFU/0.5 ml/rat) | Drug | MIC (µg/ml) | $ED_{50}$ (mg/kg) |
|---|---|---|---|---|
| *streptococcus pneumoniae$_3$* | $6.4 \times 10^4$ | isovalerylspiramycin III | 0.12 | 8.99 |
| | | crystal of isovalerylspiramycin III | 0.12 | 6.45 |
| | | carrimychin | 0.12 | 10.41 |
| | | azithromycin | 0.12 | 18.29 |
| | | acetyl spiramycin | 0.5 | 66.96 |
| | | erythrocin | 1 | 85.08 |
| *streptococcus pneumoniae$_{18}$* | $9.6 \times 10^4$ | isovalerylspiramycin III | 0.03 | 8.98 |
| | | crystal of isovalerylspiramycin III | 0.03 | 8.68 |
| | | carrimychin | 0.03 | 10.06 |
| | | azithromycin | 0.06 | 14.87 |
| | | acetyl spiramycin | 0.06 | 37.93 |
| | | erythrocin | 0.06 | 57.08 |
| *streptococcus pneumoniae$_{57}$* | $8.8 \times 10^4$ | isovalerylspiramycin III | 0.06 | 13.10 |
| | | crystal of isovalerylspiramycin III | 0.06 | 11.08 |
| | | carrimychin | 0.12 | 16.02 |
| | | azithromycin | 0.12 | 19.02 |
| | | acetyl spiramycin | 1 | 398.01 |
| | | erythrocin | 0.25 | 102.33 |
| *pyogenic streptococcus$_{772}$* | $6.9 \times 10^3$ | isovalerylspiramycin III | 0.06 | 24.61 |
| | | crystal of isovalerylspiramycin III | 0.06 | 22.81 |
| | | carrimychin | 0.12 | 26.30 |
| | | azithromycin | 0.25 | 46.89 |
| | | acetyl spiramycin | 0.25 | 98.11 |
| | | erythrocin | 0.5 | 101.33 |
| *pyogenic streptococcus$_{102}$* | $7.8 \times 10^4$ | isovalerylspiramycin III | 0.12 | 63.21 |
| | | crystal of isovalerylspiramycin III | 0.12 | 52.91 |
| | | carrimychin | 0.25 | 87.84 |
| | | azithromycin | 0.5 | 159.06 |
| | | acetyl spiramycin | 0.5 | 227.07 |
| | | erythrocin | 0.5 | 361.01 |
| *pyogenic streptococcus$_{119}$* | $4.9 \times 10^4$ | isovalerylspiramycin III | 0.12 | 52.77 |
| | | crystal of isovaletylspiramycin III | 0.12 | 49.94 |
| | | carrimychin | 0.25 | 68.48 |
| | | azithromycin | 0.25 | 68.48 |
| | | acetyl spiramycin | 0.5 | 117.53 |
| | | erythrocin | 0.5 | 233.72 |

TABLE 8

Comparison of curative effects of 5 antibiotics on mouse with abdominal infection of *enterococcus* and *staphylococcus aureus*

| Test organism | Challenging dose (CFU/0.5 ml/rat) | Drug | MIC (µg/ml) | $ED_{50}$ (mg/kg) |
|---|---|---|---|---|
| *enterococcus$_{32}$* | $5.4 \times 10^4$ | isovalerylspiramycin III | 0.25 | 70.16 |
| | | crystal of isovalerylspiramycin III | 0.25 | 65.89 |
| | | carrimychin | 0.5 | 89.29 |
| | | azithromycin | 1 | 146.51 |
| | | acetyl spiramycin | 1 | 130.34 |
| | | erythrocin | 2 | 175.23 |
| *staphylococcus aureus$_{16}$* | $5.2 \times 10^3$ | isovalerylspiramycin III | 0.25 | 20.87 |
| | | crystal of isovalerylspiramycin III | 0.25 | 19.29 |
| | | carrimychin | 0.5 | 31.98 |
| | | azithromycin | 0.5 | 31.98 |
| | | acetyl spiramycin | 1 | 43.58 |
| | | erythrocin | 1 | 82.36 |

TABLE 8-continued

Comparison of curative effects of 5 antibiotics on mouse with abdominal infection of *enterococcus* and *staphylococcus aureus*

| Test organism | Challenging dose (CFU/0.5 ml/rat) | Drug | MIC (μg/ml) | $ED_{50}$ (mg/kg) |
|---|---|---|---|---|
| *staphylococcus aureus*₇₆ | $5.8 \times 10^4$ | isovalerylspiramycin III | 0.25 | 22.26 |
| | | crystal of isovalerylspiramycin III | 0.25 | 18.71 |
| | | carrimychin | 0.5 | 31.50 |
| | | azithromycin | 1 | 58.79 |
| | | acetyl spiramycin | 1 | 66.63 |
| | | erythrocin | 1 | 64.17 |
| *staphylococcus aureus*₁₂ | $4.8 \times 10^4$ | isovalerylspiramycin III | 1 | 108.04 |
| | | crystal of isovalerylspiramycin III | 1 | 105.24 |
| | | carrimychin | 2 | 120.35 |
| | | azithromycin | 2 | 120.35 |
| | | acetyl spiramycin | 2048 | >500 |
| | | erythrocin | 256 | 266.11 |
| *staphylococcus aureus*₂₁ | $4.2 \times 10^4$ | isovalerylspiramycin III | 0.5 | 38.90 |
| | | crystal of isovalerylspiramycin III | 0.5 | 36.09 |
| | | carrimychin | 1 | 59.30 |
| | | azithromycin | 4 | 142.99 |
| | | acetyl spiramycin | 2048 | >500 |
| | | erythrocin | 4 | 213.67 |

Results of In Vivo Test:

Refer to Table 7 and Table 8 for the curative effects of the crystalline compound of isovalerylspiramycin III on mouse infected with 12 strains of bacteria, which shows a good protective effect, an effect better than isovalerylspiramycin III.

The same test is conducted for crystalline compound of levoisovalerylspiramycin III or preparations of crystalline compound of levoisovalerylspiramycin III prepared in other embodiments of the present invention, the results are similar.

Test Example 5 In Vitro Pharmacodynamic Test:

I. Determination of Clinical Isolates:

Test method: agar double dilution method: quantitatively pour the melting agar medium into a plate containing series drug concentration to blend with the drug liquid (add 5% defidrinated sheep blood to *streptococcus* and *enterococcus* to obtain a blood medium; add 7% defidrinated sheep blood to *hemophilus influenza* and add 7% defidrinated sheep blood to gonococcus medium to obtain a chocolate medium); after the mixture is solidified, it is diluted to $10^6 CFU/mL$ with fresh bacteria culture liquid, then inoculated by multi-point inoculation instrument to the agar plate containing antibacterial agents to be cultured for 18 h at 37□; putting the gonococcus to a 5% $CO_2$ incubator to be cultured for 24 h; putting the *legionella* to a 5% $CO_2$ incubator to be cultured for 48 h; putting the anaerobic bacteria to an anaerobic box to be cultured for 48 h at 37□. Observe the minimum concentration of the antibacterial drugs to inhibit the growth of bacteria, i.e. minimum inhibitory concentration (MIC), and calculate drugs $MIC_{50}$ and $MIC_{90}$ and compare them with the control drugs.

Note: $MIC_{50}$ stands for a minimum inhibitory concentration for inhabitation of 50% bacterial growth;

$MIC_{90}$ stands for a minimum inhibitory concentration for the inhabitation of 90% bacterial growth.

See Table 9 for the Test Results:

TABLE 9

Comparison on the sensitive distribution of clinic isolates between isovalerylspiramycin I, II, III and other antibiotics

| Type and strain number of the bacterium | Drug | MIC range (μg/ml) | $MIC_{50}$ (μg/ml) | $MIC_{90}$ (μg/ml) |
|---|---|---|---|---|
| *streptococcus pneumoniae* (112) | isovalerylspiramycin I | 0.005->32 | 0.12 | 2 |
| | isovalerylspiramycin II | 0.005->32 | 0.12 | 2 |
| | isovalerylspiramycin III | 0.005->64 | 0.12 | 4 |
| | carrimychin | 0.005->64 | 0.12 | 4 |
| | azithromycin | 0.005->64 | 0.25 | 8 |
| | acetyl spiramycin | 0.005->64 | 0.12 | >64 |
| | erythrocin | 0.005->64 | 0.25 | 64 |
| *pyogenic streptococcus* (93) | isovalerylspiramycin I | 0.06->32 | 0.25 | 32 |
| | isovalerylspiramycin II | 0.06->32 | 0.25 | 32 |
| | isovalerylspiramycin III | 0.06->32 | 0.25 | 32 |
| | carrimychin | 0.06->64 | 0.25 | 64 |
| | azithromycin | 0.25->64 | 0.5 | >64 |
| | acetyl spiramycin | 0.005->64 | 0.25 | >64 |
| | erythrocin | 0.06->64 | 0.5 | >64 |
| *enterococcus* (106) | isovalerylspiramycin I | 0.12->32 | 1 | 32 |
| | isovalerylspiramycin II | 0.12->32 | 1 | 16 |
| | isovalerylspiramycin III | 0.12->64 | 2 | 64 |
| | carrimychin | 0.5->64 | 2 | 64 |
| | azithromycin | 0.25->64 | 8 | >64 |
| | acetyl spiramycin | 0.12->64 | 4 | >64 |
| | erythrocin | 0.5->64 | 4 | >64 |
| *staphylococcus aureus* (155) | isovalerylspiramycin I | 0.06->64 | 1 | 64 |
| | isovalerylspiramycin II | 0.06->64 | 1 | 32 |
| | isovalerylspiramycin III | 0.06->64 | 2 | 32 |
| | carrimychin | 0.06->64 | 2 | 64 |
| | azithromycin | 0.5->64 | 2 | >64 |
| | acetyl spiramycin | 0.12->64 | 64 | >64 |
| | erythrocin | 0.12->64 | 1 | >64 |
| *S. epidermidis* (115) | isovalerylspiramycin I | 0.12->32 | 1 | 32 |
| | isovalerylspiramycin II | 0.12->64 | 1 | 64 |
| | isovalerylspiramycin III | 0.12->32 | 1 | 32 |
| | carrimychin | 0.12->64 | 2 | >64 |
| | azithromycin | 0.12->64 | 8 | >64 |
| | acetyl spiramycin | 0.03->64 | 64 | >64 |
| | erythrocin | 0.06->64 | 8 | >64 |
| *hemophilus influenzae* (37) | isovalerylspiramycin I | 0.03-32 | 0.12 | 1 |
| | isovalerylspiramycin II | 0.03-32 | 0.12 | 1 |
| | isovalerylspiramycin III | 0.03-32 | 0.12 | 1 |
| | carrimychin | 0.03-32 | 0.12 | 1 |
| | azithromycin | 0.03->64 | 0.25 | 2 |

TABLE 9-continued

Comparison on the sensitive distribution of clinic isolates between isovalerylspiramycin I, II, III and other antibiotics

| Type and strain number of the bacterium | Drug | MIC range (μg/ml) | MIC$_{50}$ (μg/ml) | MIC$_{90}$ (μg/ml) |
|---|---|---|---|---|
| gonococcus (10) | acetyl spiramycin | 0.03->64 | 0.12 | 4 |
| | erythrocin | 0.03->64 | 0.06 | 32 |
| | isovalerylspiramycin I | 0.12-16 | 1 | 4 |
| | isovalerylspiramycin II | 0.12-16 | 1 | 4 |
| | isovalerylspiramycin III | 0.12-16 | 1 | 4 |
| | carrimychin | 0.12-16 | 2 | 8 |
| | azithromycin | 0.12-64 | 2 | 8 |
| | acetyl spiramycin | 0.12-64 | 4 | 8 |
| | erythrocin | 0.12-64 | 1 | 8 |

II. Determination of *Chlamydia Trachomatis* and *Chlamydia Pneumoniae* In Vitro Test Methods:

1. Implanting HEp-2 and McCoy cell lines respectively in 96-pore culture plate (Costar Company) under 37□ and 5% $CO_2$ environment to be cultured for 48 hours, to obtain monolayer cells.

2. Diluting strains to be inoculated to 10000~20000 ifu (inclusion-forming units)/ml, 0.1 ml/pore for inoculation. Inoculating *Chlamydia Trachomatis* serotype B/TW-5/OT and D/UW-3/Cx on McCoy cell culture plate and *Chlamydia Pneumoniae* CWL-029 on HEp-2 cell culture plate. Firstly, absorb the cell culture liquid in 96-pore culture plate, and inoculate as per the standard of 0.1 ml/pore. Wherein, 4 pores A11-D11 and 2 pores C12 and D12 will not be inoculated.

3. After inoculation, use the J-6MC centrifugal machine of Beckman-Coulter Company to centrifuge the 96-pore cell culture plate with a centrifugal force×1500 g, a centrifugal temperature 35□ and a centrifugal time of 60 minutes.

4. After centrifugation, absorbing inoculated *Chlamydia Trachomatis* or *Chlamydia Pneumoniae*, and respectively adding 4 kinds of serial dilution antibiotics, 0.1 ml/pore.

5. Culturing on drug sensitive test plate of *Chlamydia Trachomatis* for 48 hours and drug sensitive test plate of *Chlamydia Pneumoniae* for 72 hours under the environment of 37□ and 5% $CO_2$. After the culture, absorbing antibiotics solution, washing for 2 times with PBS (0.01M, pH 7.4), and keeping 100% methyl alcohol for 15 minutes under room temperature.

6. Indirect immunofluorescence staining identification: respectively adding purified *Chlamydia Trachomatis* monoclonal antibody (N54 clone) and *Chlamydia Pneumoniae* monoclonal antibody (P33 clone) to the drug sensitive test plates of *Chlamydia Trachomatis* and *Chlamydia Pneumoniae*, 50 μl/pore; incubating for 30 minutes in a wet box under 37□; then, using the plate washer to wash the plates 4 times, then adding rabbit anti-mouse fluorescence antibodies (Sigma Company), 50 μl/pore; incubating and washing by the same way under the same conditions. Add mounting glycerol, 100 μl/pore; finally, observe the results under the Nikon inverted fluorescence microscope (Diaphot-200).

7. Definition of MIC: It refers to the minimal antibiotic diluted concentration that makes the growth of *Chlamdia Trachomatis* or *Chlamdia Pneumoniae* incursion bodies in 96-pore test plates completely suppressed (No fluorescence staining incursion is found in pores).

TABLE 10

Comparison on the MIC of 5 kinds of macrolide antibiotics on *Chlamydia Trachomatis* and *Chlamydia Pneumoniae* in in-vitro effect

| | Levoisovaleryl-spiramycin I (Embodiment 1) | Levoisovaleryl-spiramycin II (Embodiment 1) | Levoisovaleryl-spiramycin III (Embodiment 1) | Carrimycin | Acetyl Spiramycin (AT-SPM) | Erythrocin (EM) | Azithromycin (AM) |
|---|---|---|---|---|---|---|---|
| *Chlamydia Trachomatis* B/TW-5/OT | 0.25 μg/ml | 0.25 μg/ml | 0.25 μg/ml | 0.25 μg/ml | 4 μg/ml | 0.5 μg/ml | 0.5 μg/ml |
| *Chlamydia Trachomatis* D/UW-3/Cx | 0.25 μg/ml | 0.25 μg/ml | 0.25 μg/ml | 0.25 μg/ml | 2 μg/ml | 0.5 μg/ml | 0.25 μg/ml |
| *Chlamydia Pneumoniae* CWL-029 | 0.016 μg/ml | 0.016 μg/ml | 0.016 μg/ml | 0.016 μg/ml | 0.5 μg/ml | ≤0.016 μg/ml | 0.032 μg/ml |

1. For *Chlamydia Trachomatis* serotype B/TW-5/OT, Levoisovalerylspiramycin I, II and III are superior to Carrimycin, Erythrocin and Azithromycin in in-vitro effect, and Acetyl Spiramycin (MIC is 4 μg/ml) is relatively poor.

2. For *Chlamydia Trachomatis* serotype D/UW-3/Cx, Levoisovalerylspiramycin I, II and III are similar to Carrimycin and Azithromycin in in-vitro effect, with MIC 0.25 μg/ml, being sensitive; Erythrocin (0.5 μg/ml) follows; and Acetyl Spiramycin (MIC is 2 μg/ml) is relatively poor;

3. For *Chlamydia Pneumoniae* CWL-029, Levoisovalerylspiramycin II and Erythrocin are most sensitive in in-vitro effect, with MIC≤0.016 μg/ml; Azithromycin, Carrimycin, Levoisovalerylspiramycin I and III are relatively sensitive; Acetyl Spiramycin (MIC 0.5 μg/ml) is relatively poor.

4. In general, the effect of Levoisovalerylspiramycin on *Chlamydia* is superior to other test drugs.

III. *Mycoplasma Urealyticum* and *Mycoplasma Pneumoniae* In Vitro

1. Test methods: adding U-PPLO 0.8 ml to each pore of aseptic 12-pore cell culture plate (adding 0.9 ml to inoculum control pore and 1.0 ml to medium control pore).

2. Add $10^4$CCU/ml Uu inoculum 0.1 ml to each experimental pore. The final dose in the pore is $10^3$CCU/ml (the medium control pore will not be added with inoculum).

3. Divide into 3 groups (100 μg/ml, 10 μg/ml and 1 μg/ml antibiotic stock solution), Use aseptic Tip to add antibiotic for test to each pore: 100 µl, 50 µl, 25 µl, 12.5 µl according to the double degradation concentration gradient. (The inoculum and medium control pores will not be added with the antibiotic, and meanwhile the antibiotic control pore is arranged.)

4. Blend all pores evenly. Seal the culture plate by tapes and place it in a 37□ box for culture.

5. On 17-24 hours after the test, observe and record the Uu growth situation. When Uu inoculum control pore presents a positive growth, the minimal antibiotic concentration, which can suppress the growth of Uu, is the MIC of sample. The MIC after the test is the final MIC (24 h).

Determine the MIC of *Mycoplasma Urealyticum* and *Mycoplasma Pneumoniae* strains for 4 times and the results are:

The MIC of Levoisovalerylspiramycin I is 0.025~0.125 µg/ml.

The MIC of Levoisovalerylspiramycin II is 0.025~0.125 µg/ml.

The MIC of Levoisovalerylspiramycin III is 0.025°-0.125 µg/ml.

The MIC of Carrimycin is 0.025~0.125 µg/ml.
The MIC of Acetyl Spiramycin is 0.5 µg/ml.
The MIC of Erythrocin is 5 µg/ml.
The MIC of Azithromycin is 0.025~0.125 m/ml.

The above results indicate that Levoisovalerylspiramycin I, II, III and Carrimycin have a favorable Uu resistant effect, which is similar to the effect of Azithromycin, superior to Acetyl Spiramycin, and the effect of Erythrocin is poorest among all samples.

The same result is conducted for Levoisovalerylspiramycin I, II, III in other embodiments of the present invention or preparations containing Levoisovalerylspiramycin I, II, III, the results are similar.

Test Example 4 Clinical Test of Levoisovalerylspiramycin I, II and III

Efficacy and safety of Levoisovalerylspiramycin I, II and III (from Embodiment 1) and Azithromycin in treating adult acute respiratory infections caused by sensitive bacteria, including acute bacterial pharyngitis, suppurative tonsillitis, acute tracheobronchitis, and mild pneumonia, etc.

Adopt a multi-center, random, two blind, double simulation control test, which is carried out in 5 hospitals concurrently according to the unified clinical testing program.

I. Subject Selection Standards

1. Patients from 18 to 65 years old (men and women);

2. Sensitive acute respiratory infections caused by sensitive bacteria include acute bacterial pharyngitis, acute suppurative tonsillitis, acute tracheobronchitis, mild pneumonia and acute nasosinusitis etc;

3. Any subject shall sign an informed consent before being selected.

4. All subjects shall be contracepted in the research period and within at least 3 months upon being dosed.

II. Subject Exclusion Standards

1. Those with hepatic or renal insufficiency (Blood Cr>1.5 mg/dl and ALT>normal upper limit)

2. The women in pregnancy or lactation

3. Those with gastrointestinal tract diseases, who cannot take drugs orally.

4. Those who take antibacterial within one week before the selection.

5. Long-term alcoholics,

According to statistics on the test results by statistics experts, the clinical efficacy (FAS) is:

The effect of Levoisovalerylspiramycin I, II, III and Azithromycin are respectively 92.30%, 92.30%, 92.30% and 89.61%.

Clearance of Pathogens:

The clearance of pathogens of Levoisovalerylspiramycin I, II, III and Azithromycin are respectively 97.56%, 97.56%, 97.56% and 92.86%.

Adverse Reaction:

The adverse reaction of Levoisovalerylspiramycin I, II, III and Azithromycin are respectively 2.5%, 2.5%, 2.5% and 7.6%.

The clinical test indicates that Levoisovalerylspiramycin I, II, III are new safe and effective anti-infection drugs.

The some test is conducted for Levoisovalerylspiramycin I, II, III in the other embodiments of the present invention or preparations containing Levoisovalerylspiramycin I, II, III, the results are similar.

The invention claimed is:

1. A levoisovalerylspiramycin, being the one of levoisovalerylspiramycin I, II or III compound, wherein, the chemical structural formula of levoisovalerylspiramycin I compound is shown as formula (I), on the condition of chloroform as solvent, temperature 25° C., and concentration 0.02 g/ml, the measured specific optical rotation $[\alpha]_D$ is −49°~−62°; and the melting point is 116~122° C.;

the chemical structural formula of levoisovalerylspiramycin II compound is shown as formula (II), on the condition of chloroform as solvent, temperature 25° C., and concentration 0.02 g/ml, the measured specific optical rotation $[\alpha]_D$ is −55°~−61°; and the melting point is 120° C.~128° C.;

the chemical structural formula of levoisovalerylspiramycin III compound is shown as formula (III), on the condition that chloroform as solvent, temperature 25° C., and concentration 0.02 g/ml, the measured specific optical rotation $[\alpha]_D$ is −49°~−51°; and the melting point is 116° C.~118° C.;

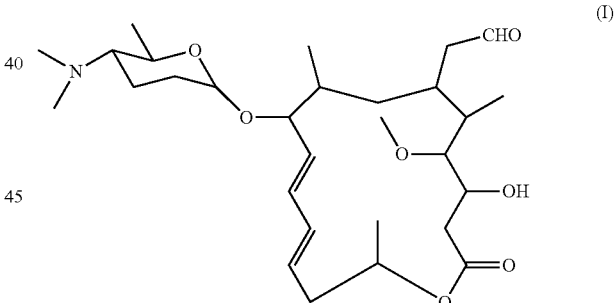

(I)

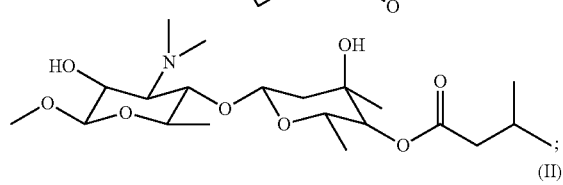

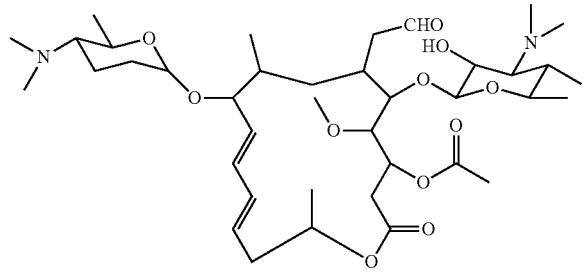

(II)

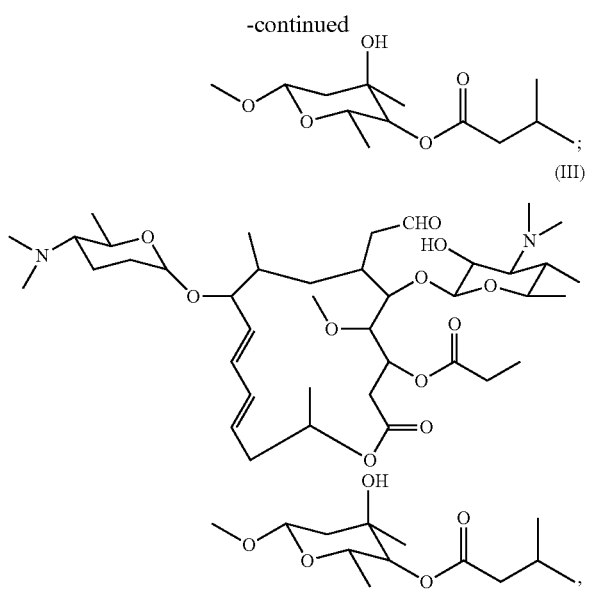

(III)

wherein:

levoisovalerylspiramycin I compound is a crystalline compound, X-ray powder diffraction of which measured by Cu-Ka ray has characteristic peaks at 2θ=7.6°, 8.0°, 10.0°, 11.4°, 16.4°, 17.0°, 17.5°, 17.9°, 19.5°, 22.7°, 23.7° and 24.4°;

levoisovalerylspiramycin II compound is a crystalline compound, X-ray powder diffraction of which measured by Cu-Ka ray has characteristic peaks at 2θ=10.0°, 11.6°, 16.4°, 17.3°, 19.1°, 21.2°, 22.1°, 22.7°, 26.4°, 26.9°, 27.5° and 31.5°;

levoisovalerylspiramycin III compound is a crystalline compound, X-ray powder diffraction of which measured by Cu-Ka ray has characteristic peaks at 2θ=8.0°, 10.0°, 11.2°, 11.7°, 16.4°, 19.1°, 19.6°, 20.0°, 21.4°, 22.9°, 23.6° and 29.4°.

2. A preparation containing the levoisovalerylspiramycin according to claim 1, wherein, the preparation contains levoisovalerylspiramycin I, pharmaceutical salt of levoisovalerylspiramycin I, levoisovalerylspiramycin I and pharmaceutically acceptable adjuvant, or pharmaceutical salt of levoisovalerylspiramycin I and pharmaceutically acceptable adjuvant, the purity of levoisovalerylspiramycin I is above 90 wt %; or the preparation contains levoisovalerylspiramycin II, pharmaceutical salt of levoisovalerylspiramycin II, levoisovalerylspiramycin II and pharmaceutically acceptable adjuvant, or pharmaceutical salt of levoisovalerylspiramycin II and pharmaceutically acceptable adjuvant, the purity of levoisovalerylspiramycin II is above 90 wt %; or the preparation contains levoisovalerylspiramycin III, pharmaceutical salt of levoisovalerylspiramycin III, levoisovalerylspiramycin III and pharmaceutically acceptable adjuvant, or pharmaceutical salt of levoisovalerylspiramycin III and pharmaceutically acceptable adjuvant, the purity of levoisovalerylspiramycin III is above 90 wt %.

3. The preparation according to claim 2, wherein: the preparation comprises the following unit dose: the content of levoisovalerylspiramycin I, II or III is respectively 10~1500 mg.

4. The preparation according to claim 2, wherein: the weight percentage of levoisovalerylspiramycin I, II or III is respectively 10~95%.

5. The preparation according to claim 2, wherein: the preparation includes solution for injection, powder for injection or lyophilized powder prepared by mixing levoisovalerylspiramycin I and at least one of citric acid, adipic acid, or maleic acid; solution for injection, powder for injection or lyophilized powder prepared by mixing levoisovalerylspiramycin II and at least one of citric acid, adipic acid, maleic acid; solution for injection, powder for injection or lyophilized powder prepared by mixing levoisovalerylspiramycin III and at least one of citric acid, adipic acid, or maleic acid.

6. A method for preparing levoisovalerylspiramycin according to claim 1, wherein, the method comprises: preparing levocarrimycin, and purifying levoisovalerylspiramycin I, II or III, wherein the process for preparing levocarrimycin includes: culturing and biologically fermenting cloned fungal strains WSP-195 produced by spiramycin containing 4"-isovaleryl transferase gene, and extracting a fermentation liquor;

fermentation proceeds on the condition of pH 6.0~9.0, the curves of pH variation with time show three continuous phases, wherein, the first phase satisfies formula $y_1=k_1x_1+6.0$, in which $0.0227 \leq k_1 \leq 0.1364, 0<x_1 \leq 22$; the second phase satisfies formula $y_2=k_2x_2+b_2$, in which $-0.0735 \leq k_2<0, 6.5<b_2 \leq 10.62, 22 \leq x_2 \leq 56$; and the third phase satisfies formula $y_3=k_3x_3+b_3$, in which $0<k_3 \leq 0.0078, 6.06 \leq b_3<6.5, 56 \leq x_3 \leq 120$, wherein, $x_1$, $x_2$ and $x_3$ represent time respectively, and $y_1$, $y_2$ and $y_3$ represent pH value respectively, and $k_1$, $k_2$, and $k_3$ are a constant respectively during each fermentation process;

a culture process of the method for preparing the levocarrimycin is: culturing the cloned fungal strains WSP-195 produced by spiramycin containing 4"-transferase gene on an agarslantculture-medium containing 2% soybean cake meal, 1% glucose, 3% starch, 0.5%$CaCO_3$, 0.4% NaCl and 2% agar for 8~15 days under pH6.5~7.5 and temperature 28~38° C., then inoculating to a seed medium containing 1.5% soybean cake meal, 3.0% starch, 0.4% NaCl, 0.5% $CaCO_3$ 0.3% fish peptone and 0.05% $KH^2PO_4$ and culturing for 40~80 hours under pH6.5~7.5 and temperature 25~30° C., implanting to a fermentation medium containing 0.5% glucose, 6.0% starch, 0.5% yeast powder, 2.0% fish meal, 0.6% $NH_4NO_3$, 1.0% NaCl, 0.5% $CaCO_3$, 0.05% $KH_9PO_4$, 0.1% $MgSO_4$, 0.5% soybean oil and 0.02% defoamer and culturing for 72~120 hours under 26~30° C., 0.1~20% inoculation amount, to obtain the fermentation liquor;

a step for extracting biological fermentation liquor includes: processing the fermentation liquor with aluminum sulfate to obtain filtrate, regulating pH of the filtrate to 8.5~9.0, using butyl acetate for extraction, cleaning butyl acetate extract with non-saline and 1%$NaH_2PO_4$, then using pH2.0~2.5 water for extraction to obtain aqueous extract, regulating pH to 4.5~5.5, volatilizing and eliminating the residual butyl acetate to obtain water extract, filtering and regulating pH to pH8.5~9.0, precipitating the filtrate and washing with purified water to obtain the wet product, and drying it to obtain levocarrimycin;

a step for purifying levoisovalerylspiramycin I, II or III includes: purifying the levocarrimycin sample with chromato graph method, performing gradient elution and separating the component target peak of levoisovalerylspiramycin I, II or III via ODS chromatographic column in acetonitrile and ammonium acetate buffer solution, in the purification of levoisovalerylspiramycin I, II or III, recording the UV spectrum diagram of levoisovalerylspiramycin I, II or III through preparative high performance liquid chromatography and UV detection, and collecting levoisovalerylspiramycin I sample based on retention time 44.759 min, levoisovalerylspiramycin II sample based on retention time 43.34 min, and levoisovalerylspiramycin III sample based on retention time 48.009 min.

7. The method according to claim 6, wherein: in the purification of levoisovalerylspiramycin I, II or III, eliminating acetonitrile in the collected levoisovalerylspiramycin I, II or III respectively with rotary evaporation method, then using ethyl acetate for extraction, eliminating ethyl acetate in the extract by evaporation to obtain paste sample;

re-dissolving the sample with petroleum ether, eliminating the petroleum ether by evaporation to respectively obtain the white power of levoisovalerylspiramycin I, II or III.

8. The method according to claim 6, wherein: a mixture of acetonitrile and 150 mM ammonium acetate solution with pH 8.5 is a mobile phase in the purification of levoisovalerylspiramycin I, II or III, the conditions required for purification of levoisovalerylspiramycin I, II or III is: linear gradient: 0~60 minutes, acetonitrile being 25% ~65%; and 61~90 minutes, acetonitrile being 65% ~90%;

flow velocity: 260 mL/min;
sample size: 10 mL;
sample concentration: 0.5 g/mL;
measurement wavelength: 231 nm;
way of collecting: collection via UV triggering.

9. The method according to claim 7, wherein the white power of levoisovalerylspiramycin I, II or III is made into crystal, wherein, a method for preparing crystalline compound of levoisovalerylspiramycin I comprises: dissolving solid levoisovalerylspiramycin I compound in a mixed solvent of ethyl acetate, absolute ethyl alcohol and anhydrous acetone, adding pure water and stirring the mixture simultaneously, cooling to 5° C. ~15° C. after addition of pure water, continuing stirring when cooling, then obtaining crystalline compound of levoisovalerylspiramycin I, wherein, a volume ratio of ethyl acetate, absolute ethyl alcohol and anhydrous acetone in the mixed solvent is 1: 0.1~10: 05~1, or a method for preparing the crystalline compound of levoisovalerylspiramycin II is: dissolving solid levoisovalerylspiramycin II compound in a mixed solvent of absolute methanol, absolute ethyl alcohol and anhydrous acetone, adding pure water and stirring the mixture simultaneously, cooling to 5° C. ~15° C. after adding pure water, continuing stirring when cooling, then obtaining crystalline compound of levoisovalerylspiramycin II, wherein, a volume ratio of absolute methanol, anhydrous acetone and absolute ethyl alcohol in the mixed solvent is 1:0.1~10:0.5~1, or the method for preparing the crystalline compound of levoisovalerylspiramycin III is: dissolving solid levoisovalerylspiramycin III compound in a mixed solvent of absolute methanol, absolute ethyl alcohol and anhydrous acetone, adding pure water and stirring the mixture simultaneously, cooling to 5° C. ~15° C. after adding pure water, continuing stirring when cooling, then obtaining crystalline compound of levoisovalerylspiramycin III, wherein, a volume ratio of absolute methanol, absolute ethyl alcohol, and anhydrous acetone in the mixed solvent is 1:0.1~10:0.5~1.

10. The method according to claim 9, wherein, in the method for preparing crystalline compound of levoisovalerylspiramycin I, the stirring rate is 30~60 r/min during adding pure water; the stirring rate is 10~30 r/min after adding pure water; and the cooling rate is 1~3° C./h after adding pure water.

11. The method according to claim 9, wherein, in the method for preparing crystalline compound of levoisovalerylspiramycin II, the stirring rate is 30~60 r/min during adding pure water; the stirring rate is 10~30 r/min after adding pure water; and the cooling rate is 1~3° C./h after adding pure water.

12. The method according to claim 9, wherein, in the method for preparing crystalline compound of levoisovalerylspiramycin III, the stirring rate is 30~60 r/min during adding pure water; the stirring rate after addition of pure water is 10~30 r/min; and the cooling rate is 1~3° C./hour after adding pure water.

13. The preparation according to claim 2, wherein, the purity of levoisovalerylspiramycin I is more than 98 wt %;

the purity of levoisovalerylspiramycin II is more than 98 wt %; or the purity of levoisovalerylspiramycin III is more than 98 wt %.

14. The preparation according to claim 3, wherein, the content of levoisovalerylspiramycin I, II or III is respectively 50~1000 mg.

15. The preparation according to claim 3, wherein, the content of levoisovalerylspiramycin I, II or III is respectively 100~500 mg.

16. The preparation according to claim 4, wherein: the weight percentage of levoisovalerylspiramycin I, II or III is respectively 75~95%.

17. The method according to claim 9, wherein, during preparing crystalline compound of levoisovalerylspiramycin I, the volume ratio of ethyl acetate, absolute ethyl alcohol and anhydrous acetone in the mixed solvent is 1:2~8:0.8~1;

during preparing crystalline compound of levoisovalerylspiramycin II, the volume ratio of absolute methanol, anhydrous acetone and absolute ethyl alcohol in the mixed solvent is 1:2~8:0.8~1; or during preparing crystalline compound of levoisovalerylspiramycin III, the volume ratio of absolute methanol, absolute ethyl alcohol, and anhydrous acetone in the mixed solvent is 1:2~8:0.8~1.

* * * * *